(12) United States Patent
Hansmann et al.

(10) Patent No.: US 9,107,590 B2
(45) Date of Patent: Aug. 18, 2015

(54) METHOD AND APPARATUS FOR DETECTING VASCULAR CONDITIONS WITH A CATHETER

(75) Inventors: Douglas R. Hansmann, Bainbridge Island, WA (US); Robert L. Wilcox, Bothell, WA (US); Peter R. Rule, Los Altos, CA (US); Francisco S. Villar, Union City, CA (US)

(73) Assignee: EKOS CORPORATION, Bothell, WA (US)

( * ) Notice: Subject to any disclaimer, the term of this patent is extended or adjusted under 35 U.S.C. 154(b) by 2418 days.

(21) Appl. No.: 11/047,363

(22) Filed: Jan. 31, 2005

(65) Prior Publication Data

US 2005/0215946 A1  Sep. 29, 2005

Related U.S. Application Data

(60) Provisional application No. 60/583,301, filed on Jun. 25, 2004, provisional application No. 60/540,703, filed on Jan. 30, 2004, provisional application No. 60/540,900, filed on Jan. 29, 2004.

(51) Int. Cl.
*A61B 5/027* (2006.01)
*A61M 25/00* (2006.01)
(Continued)

(52) U.S. Cl.
CPC .............. *A61B 5/027* (2013.01); *A61B 5/028* (2013.01); *A61B 8/0808* (2013.01); *A61B 17/2202* (2013.01); *A61M 37/0092* (2013.01); *A61N 7/022* (2013.01); *A61B 8/06* (2013.01); *A61B 17/221* (2013.01); *A61B 2017/00022* (2013.01); *A61B 2017/00057* (2013.01); *A61B 2017/00061* (2013.01); *A61B 2017/00084* (2013.01);
(Continued)

(58) Field of Classification Search
CPC ................. A61B 17/2202; A61B 2017/00022; A61B 2017/00084; A61B 2017/22084; A61B 5/027; A61M 37/0092; A61N 7/022
USPC ..................................... 604/66, 22, 15; 606/41
See application file for complete search history.

(56) References Cited

U.S. PATENT DOCUMENTS 3,430,625 A  3/1969  McLeod, Jr.
3,443,226 A  5/1969  Knight
(Continued)

FOREIGN PATENT DOCUMENTS

EP  0744189  11/1996
EP  1 090 658 A1  4/2001
(Continued)

OTHER PUBLICATIONS

Apr. 1, 2009 Supplementary European Search Report, Application No. EP 05 71 2272, 4 pages.
(Continued)

*Primary Examiner* — Nicholas Lucchesi
*Assistant Examiner* — Weng Lee
(74) *Attorney, Agent, or Firm* — Knobbe, Martens, Olson & Bear, LLP

(57) ABSTRACT

A method for treating an occlusion comprises positioning a catheter at a treatment site in a patient's vasculature. A blockage is located at the treatment site. The method further comprises performing a medical treatment at the treatment site. The medical treatment is configured to reduce the blockage. The method further comprises making a plurality of measurements at the treatment site.

8 Claims, 29 Drawing Sheets

(51) Int. Cl.
*A61M 37/00* (2006.01)
*A61N 7/02* (2006.01)
*A61B 5/028* (2006.01)
*A61B 17/22* (2006.01)
*A61B 8/08* (2006.01)
*A61B 8/06* (2006.01)
*A61B 17/221* (2006.01)
*A61B 17/00* (2006.01)

(52) U.S. Cl.
CPC ... *A61B2017/22084* (2013.01); *A61M 25/0045* (2013.01); *A61M 25/0068* (2013.01); *A61M 25/0082* (2013.01)

(56) References Cited

U.S. PATENT DOCUMENTS

| | | |
|---|---|---|
| 3,565,062 A | 2/1971 | Kuris |
| 3,827,115 A | 8/1974 | Bom |
| 3,941,122 A | 3/1976 | Jones |
| 4,192,294 A | 3/1980 | Gekhman et al. |
| 4,309,989 A | 1/1982 | Fahim |
| 4,319,580 A | 3/1982 | Colley |
| 4,354,502 A | 10/1982 | Colley et al. |
| 4,754,752 A | 7/1988 | Ginsburg et al. |
| 4,821,740 A | 4/1989 | Tachibana et al. |
| 4,870,953 A | 10/1989 | Donmicheal et al. |
| 4,921,478 A | 5/1990 | Solano et al. |
| 4,936,281 A | 6/1990 | Stasz |
| 4,948,587 A | 8/1990 | Kost et al. |
| 4,951,677 A | 8/1990 | Crowley et al. |
| 4,953,565 A | 9/1990 | Tachibana et al. |
| 4,960,109 A | 10/1990 | Lele |
| 4,971,991 A | 11/1990 | Umemura et al. |
| 5,059,851 A | 10/1991 | Corl et al. |
| 5,088,499 A | 2/1992 | Unger |
| 5,108,369 A | 4/1992 | Ganguly et al. |
| 5,129,883 A | 7/1992 | Black |
| 5,149,319 A | 9/1992 | Unger |
| 5,158,071 A | 10/1992 | Umemura et al. |
| 5,163,421 A | 11/1992 | Bernstein et al. |
| 5,163,436 A | 11/1992 | Hashimoto et al. |
| 5,178,620 A | 1/1993 | Eggers et al. |
| 5,185,071 A | 2/1993 | Serwer et al. |
| 5,197,946 A | 3/1993 | Tachibana |
| 5,226,421 A | 7/1993 | Frisbie et al. |
| 5,267,954 A | 12/1993 | Nita |
| 5,269,291 A | 12/1993 | Carter |
| 5,271,406 A | 12/1993 | Ganguly et al. |
| 5,279,546 A | 1/1994 | Mische et al. |
| 5,307,816 A | 5/1994 | Hashimoto |
| 5,312,328 A | 5/1994 | Nita et al. |
| 5,315,998 A | 5/1994 | Tachibana et al. |
| 5,318,014 A | 6/1994 | Carter |
| 5,342,292 A | 8/1994 | Nita et al. |
| 5,344,395 A | 9/1994 | Whalen et al. |
| 5,345,940 A | 9/1994 | Seward et al. |
| 5,351,693 A | 10/1994 | Taimisto et al. |
| 5,362,309 A | 11/1994 | Carter |
| 5,368,036 A | 11/1994 | Tanaka et al. |
| 5,368,557 A | 11/1994 | Nita et al. |
| 5,368,558 A | 11/1994 | Nita |
| 5,370,675 A | 12/1994 | Edwards et al. |
| 5,372,138 A | 12/1994 | Crowley et al. |
| 5,380,273 A | 1/1995 | Dubrul et al. |
| 5,399,158 A | 3/1995 | Lauer et al. |
| 5,401,237 A | 3/1995 | Tachibana et al. |
| 5,405,322 A | 4/1995 | Lennox et al. |
| 5,431,663 A | 7/1995 | Carter |
| 5,440,914 A | 8/1995 | Tachibana et al. |
| 5,447,509 A | 9/1995 | Mills et al. |
| 5,447,510 A | 9/1995 | Jensen |
| 5,453,575 A | 9/1995 | O'Donnell et al. |
| 5,456,259 A | 10/1995 | Barlow et al. |
| 5,474,531 A | 12/1995 | Carter |
| 5,509,896 A | 4/1996 | Carter |
| 5,523,058 A | 6/1996 | Umemura et al. |
| 5,533,986 A | 7/1996 | Mottola et al. |
| 5,542,917 A | 8/1996 | Nita et al. |
| 5,542,935 A | 8/1996 | Unger et al. |
| 5,558,092 A | 9/1996 | Unger et al. |
| 5,560,362 A | 10/1996 | Sliwa, Jr. et al. |
| 5,569,197 A | 10/1996 | Helmus et al. |
| 5,582,586 A | 12/1996 | Tachibana et al. |
| 5,588,432 A | 12/1996 | Crowley |
| 5,603,694 A | 2/1997 | Brown et al. |
| 5,620,409 A | 4/1997 | Gans et al. |
| 5,620,479 A | 4/1997 | Diederich |
| 5,624,382 A | 4/1997 | Oppelt |
| 5,628,728 A | 5/1997 | Tachibana et al. |
| 5,630,837 A | 5/1997 | Crowley |
| 5,648,098 A | 7/1997 | Porter |
| 5,660,909 A | 8/1997 | Tachibana et al. |
| 5,681,296 A | 10/1997 | Ishida |
| 5,695,460 A | 12/1997 | Siegel et al. |
| 5,697,897 A | 12/1997 | Buchholtz et al. |
| 5,713,831 A | 2/1998 | Olsson |
| 5,713,848 A | 2/1998 | Dubrul et al. |
| 5,720,710 A | 2/1998 | Tachibana et al. |
| 5,724,976 A | 3/1998 | Hirama et al. |
| 5,725,494 A | 3/1998 | Brisken |
| 5,728,062 A | 3/1998 | Brisken |
| 5,733,315 A | 3/1998 | Burdette et al. |
| 5,735,811 A | 4/1998 | Brisken |
| 5,752,930 A | 5/1998 | Baudino et al. |
| 5,775,338 A | 7/1998 | Hastings |
| 5,817,021 A | 10/1998 | Reichenberger |
| 5,823,962 A | 10/1998 | Lerch et al. |
| 5,827,203 A | 10/1998 | Nita |
| 5,834,880 A | 11/1998 | Lewandowski et al. |
| 5,836,440 A | 11/1998 | Mindich |
| 5,836,896 A | 11/1998 | Rosenschein |
| 5,836,940 A | 11/1998 | Gregory |
| 5,840,031 A | 11/1998 | Crowley |
| 5,846,218 A | 12/1998 | Brisken et al. |
| 5,876,345 A | 3/1999 | Eaton et al. |
| 5,895,398 A | 4/1999 | Wensel et al. |
| 5,916,192 A | 6/1999 | Nita et al. |
| 5,925,016 A | 7/1999 | Chornenky et al. |
| 5,928,186 A | 7/1999 | Homsma et al. |
| 5,931,805 A | 8/1999 | Brisken |
| 5,935,124 A | 8/1999 | Klumb et al. |
| 5,938,595 A | 8/1999 | Glass et al. |
| 5,941,868 A | 8/1999 | Kaplan et al. |
| 5,941,896 A * | 8/1999 | Kerr .......................... 606/200 |
| 5,957,851 A | 9/1999 | Hossack |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,997,497 A | 12/1999 | Nita et al. |
| 6,001,069 A * | 12/1999 | Tachibana et al. ................. 601/2 |
| 6,004,269 A | 12/1999 | Crowley et al. |
| 6,024,703 A | 2/2000 | Zanelli et al. |
| 6,024,718 A | 2/2000 | Chen et al. |
| 6,027,515 A | 2/2000 | Cimino |
| 6,033,397 A | 3/2000 | Laufer et al. |
| 6,053,868 A | 4/2000 | Geistert et al. |
| 6,063,069 A | 5/2000 | Cragg et al. |
| 6,066,123 A | 5/2000 | Bednarski et al. |
| 6,078,830 A | 6/2000 | Levin et al. |
| 6,088,613 A | 7/2000 | Unger |
| 6,089,573 A | 7/2000 | Udagawa |
| 6,096,000 A | 8/2000 | Tachibana et al. |
| 6,110,098 A | 8/2000 | Renirie et al. |
| 6,110,314 A | 8/2000 | Nix et al. |
| 6,113,546 A | 9/2000 | Suorsa et al. |
| 6,113,558 A | 9/2000 | Rosenschein et al. |
| 6,113,570 A | 9/2000 | Siegel et al. |
| 6,117,101 A | 9/2000 | Diederich et al. |
| 6,120,454 A | 9/2000 | Suorsa et al. |
| 6,135,971 A | 10/2000 | Hutchinson et al. |
| 6,135,976 A | 10/2000 | Tachibana et al. |
| 6,149,596 A | 11/2000 | Bancroft |

(56) References Cited

U.S. PATENT DOCUMENTS

| | | |
|---|---|---|
| 6,176,842 B1 | 1/2001 | Tachibana et al. |
| 6,196,973 B1 | 3/2001 | Lazenby et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,287,271 B1 | 9/2001 | Dubrul et al. |
| 6,296,619 B1 | 10/2001 | Brisken et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,361,500 B1 | 3/2002 | Masters |
| 6,361,554 B1 | 3/2002 | Brisken |
| 6,366,719 B1 | 4/2002 | Heath et al. |
| 6,372,498 B2 | 4/2002 | Newman et al. |
| 6,387,052 B1 | 5/2002 | Quinn et al. |
| 6,391,042 B1 | 5/2002 | Cimino |
| 6,394,997 B1 | 5/2002 | Lemelson |
| 6,398,772 B1 | 6/2002 | Bond et al. |
| 6,416,740 B1 | 7/2002 | Unger |
| 6,423,026 B1 | 7/2002 | Gesswein et al. |
| 6,433,464 B2 | 8/2002 | Jones |
| 6,437,487 B1 | 8/2002 | Mohr, III et al. |
| 6,461,586 B1 | 10/2002 | Unger |
| 6,464,680 B1 | 10/2002 | Brisken et al. |
| 6,471,683 B2 | 10/2002 | Drasier et al. |
| 6,478,765 B2 | 11/2002 | Siegel et al. |
| 6,485,430 B1 | 11/2002 | Quinn et al. |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,537,224 B2 | 3/2003 | Mauchamp et al. |
| 6,542,767 B1 | 4/2003 | McNichols et al. |
| 6,551,337 B1 | 4/2003 | Rabiner et al. |
| 6,558,366 B1 | 5/2003 | Drasler et al. |
| 6,561,998 B1 | 5/2003 | Roth et al. |
| 6,562,021 B1 | 5/2003 | Derbin et al. |
| 6,565,552 B1 | 5/2003 | Barbut |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,582,392 B1 | 6/2003 | Bennett et al. |
| 6,585,763 B1 | 7/2003 | Keilman et al. |
| 6,589,182 B1 | 7/2003 | Loftman et al. |
| 6,605,084 B2 | 8/2003 | Acker et al. |
| 6,607,502 B1 | 8/2003 | Maguire et al. |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,536 B2 | 11/2003 | Mathews et al. |
| 6,652,547 B2 | 11/2003 | Rabiner et al. |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,723,063 B1 | 4/2004 | Zhang et al. |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,767,345 B2 | 7/2004 | St. Germain et al. |
| 6,794,369 B2 | 9/2004 | Newman et al. |
| 6,824,575 B1 | 11/2004 | Otomo et al. |
| 6,830,577 B2 | 12/2004 | Nash et al. |
| 6,849,062 B2 | 2/2005 | Kantor |
| 6,855,123 B2 | 2/2005 | Nita |
| 6,866,670 B2 | 3/2005 | Rabiner et al. |
| 6,905,505 B2 | 6/2005 | Dodson, Jr. et al. |
| 6,921,371 B2 | 7/2005 | Wilson |
| 6,929,633 B2 | 8/2005 | Evans et al. |
| 6,942,620 B2 | 9/2005 | Nita et al. |
| 6,945,937 B2 | 9/2005 | Culp et al. |
| 6,958,040 B2 | 10/2005 | Oliver et al. |
| 6,979,293 B2 | 12/2005 | Hansmann et al. |
| 6,985,771 B2 | 1/2006 | Fischell et al. |
| 7,077,820 B1 | 7/2006 | Kadziauskas et al. |
| 7,137,963 B2 | 11/2006 | Nita et al. |
| 7,141,044 B2 | 11/2006 | Gentsler |
| 7,166,098 B1 | 1/2007 | Steward et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,309,334 B2 | 12/2007 | von Hoffmann |
| 7,335,180 B2 | 2/2008 | Nita et al. |
| 7,341,569 B2 | 3/2008 | Soltani et al. |
| 7,503,895 B2 | 3/2009 | Rabiner et al. |
| 7,540,852 B2 | 6/2009 | Nita et al. |
| 7,567,016 B2 | 7/2009 | Lu et al. |
| 7,604,608 B2 | 10/2009 | Nita et al. |
| 7,621,902 B2 | 11/2009 | Nita et al. |
| 7,758,509 B2 | 7/2010 | Angelsen et al. |
| 7,771,372 B2 | 8/2010 | Wilson |
| 7,789,830 B2 | 9/2010 | Fujita et al. |
| 7,828,754 B2 | 11/2010 | Abe et al. |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita et al. |
| 2001/0007940 A1 | 7/2001 | Tu et al. |
| 2001/0025190 A1 | 9/2001 | Weber et al. |
| 2001/0037106 A1 | 11/2001 | Shadduck |
| 2001/0039419 A1 | 11/2001 | Francischelli et al. |
| 2002/0000763 A1 | 1/2002 | Jones |
| 2002/0019644 A1 | 2/2002 | Hastings et al. |
| 2002/0032394 A1 | 3/2002 | Brisken et al. |
| 2002/0045890 A1 | 4/2002 | Celliers et al. |
| 2002/0052620 A1 | 5/2002 | Barbut |
| 2002/0068869 A1 | 6/2002 | Brisken et al. |
| 2002/0077550 A1 | 6/2002 | Rabiner et al. |
| 2002/0082238 A1 | 6/2002 | Newman et al. |
| 2002/0123787 A1 | 9/2002 | Weiss |
| 2002/0133111 A1* | 9/2002 | Shadduck ............. 604/19 |
| 2002/0193708 A1 | 12/2002 | Thompson et al. |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0109812 A1 | 6/2003 | Corl et al. |
| 2003/0114761 A1* | 6/2003 | Brown ............. 600/474 |
| 2003/0135262 A1 | 7/2003 | Dretler |
| 2003/0163147 A1 | 8/2003 | Hare et al. |
| 2003/0220568 A1 | 11/2003 | Hansmann et al. |
| 2003/0236539 A1 | 12/2003 | Rabiner et al. |
| 2004/0001809 A1 | 1/2004 | Brisken et al. |
| 2004/0015061 A1* | 1/2004 | Currier et al. ............. 600/310 |
| 2004/0015138 A1 | 1/2004 | Currier et al. |
| 2004/0019318 A1 | 1/2004 | Wilson et al. |
| 2004/0024347 A1 | 2/2004 | Wilson et al. |
| 2004/0024393 A1 | 2/2004 | Nita et al. |
| 2004/0039311 A1 | 2/2004 | Nita et al. |
| 2004/0049148 A1 | 3/2004 | Rodriguez et al. |
| 2004/0059313 A1 | 3/2004 | Anderson et al. |
| 2004/0068189 A1 | 4/2004 | Wilson et al. |
| 2004/0082857 A1 | 4/2004 | Schonenberger et al. |
| 2004/0097996 A1 | 5/2004 | Hare et al. |
| 2004/0138570 A1 | 7/2004 | Nita et al. |

(56) References Cited

U.S. PATENT DOCUMENTS

| | | |
|---|---|---|
| 2004/0162571 A1 | 8/2004 | Rabiner et al. |
| 2004/0171981 A1 | 9/2004 | Buffen et al. |
| 2004/0199228 A1 | 10/2004 | Wilson |
| 2004/0220514 A1 | 11/2004 | Cafferata |
| 2004/0236350 A1 | 11/2004 | Bolduc et al. |
| 2004/0243062 A1 | 12/2004 | Henry |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043629 A1 | 2/2005 | Rabiner et al. |
| 2005/0043753 A1 | 2/2005 | Rabiner et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0192556 A1 | 9/2005 | Soltani et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0256410 A1 | 11/2005 | Rabiner et al. |
| 2006/0069303 A1 | 3/2006 | Couvillon |
| 2006/0106308 A1 | 5/2006 | Hansmann et al. |
| 2006/0116610 A1 | 6/2006 | Hare et al. |
| 2006/0173387 A1 | 8/2006 | Hansmann et al. |
| 2006/0184070 A1 | 8/2006 | Hansmann et al. |
| 2007/0037119 A1 | 2/2007 | Pal et al. |
| 2007/0066978 A1 | 3/2007 | Schafer et al. |
| 2007/0225619 A1 | 9/2007 | Rabiner et al. |
| 2007/0239027 A1 | 10/2007 | Nita |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 10/2008 | Unger |
| 2008/0306499 A1 | 12/2008 | Katoh et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0112150 A1 | 4/2009 | Unger et al. |
| 2009/0216246 A1 | 8/2009 | Nita et al. |
| 2010/0010393 A1 | 1/2010 | Duffy et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0204642 A1 | 8/2010 | Wilson et al. |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2011/0160621 A1 | 6/2011 | Nita |
| 2011/0201974 A1 | 8/2011 | Hansmann et al. |
| 2011/0288449 A1 | 11/2011 | Schenkengel |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Okuno et al. |
| 2012/0179073 A1 | 7/2012 | Nita |
| 2012/0197277 A1 | 8/2012 | Stinis |

FOREIGN PATENT DOCUMENTS

| | | |
|---|---|---|
| JP | H02-180275 | 7/1990 |
| JP | 2001-340336 | 12/2001 |
| JP | 2002-136537 | 5/2002 |
| WO | WO 92/07622 | 5/1992 |
| WO | WO 96/27341 | 9/1996 |
| WO | WO 96/29935 | 10/1996 |
| WO | WO 96/36286 | 11/1996 |
| WO | WO 97/19645 | 5/1997 |
| WO | WO 97/27808 | 8/1997 |
| WO | WO 98/11826 | 3/1998 |
| WO | WO 98/18391 | 5/1998 |
| WO | WO 98/48711 | 11/1998 |
| WO | WO 99/32184 | 7/1999 |
| WO | WO 99/33500 | 7/1999 |
| WO | WO 99/34858 | 7/1999 |
| WO | WO 99/39647 | 8/1999 |
| WO | WO 99/42039 | 8/1999 |
| WO | WO 99/44512 | 9/1999 |
| WO | WO 00/00095 | 1/2000 |
| WO | WO 00/38580 | 7/2000 |
| WO | WO 00/69341 | 11/2000 |
| WO | WO 01/13357 | 2/2001 |
| WO | WO 01/74255 | 10/2001 |
| WO | WO 01/87174 A1 | 11/2001 |
| WO | WO 01/95788 | 12/2001 |
| WO | WO 02/13678 | 2/2002 |
| WO | WO 02/15803 | 2/2002 |
| WO | WO 02/15804 | 2/2002 |
| WO | WO 03/051208 | 6/2003 |
| WO | WO 03/051208 A1 | 6/2003 |
| WO | WO 2005/027756 | 3/2005 |
| WO | WO 2005/084552 | 9/2005 |
| WO | WO 2005/084553 | 9/2005 |

OTHER PUBLICATIONS

International Search Report; PCT/US05/02765.

Schafer et al., "Influence of Ultrasound Operating Parameters on Ultrasound-Induced Thrombolysis in Vitro"; Ultrasound in Med. & Biol., vol. 31, No. 6, pp. 841-847; 2005.

Tsetis et al., "Potential Benefits From Heating the High-Dose Rtpa Boluses Used in Catheter-Directed Thrombolysis for Acute/Subacute Lower Limb Ischemia", J Endovasc. Ther. 10:739-744 (2003).

International Search Report and Written Opinion for International Application No. PCT/US2005/002765, mailed Jul. 20, 2006.

* cited by examiner

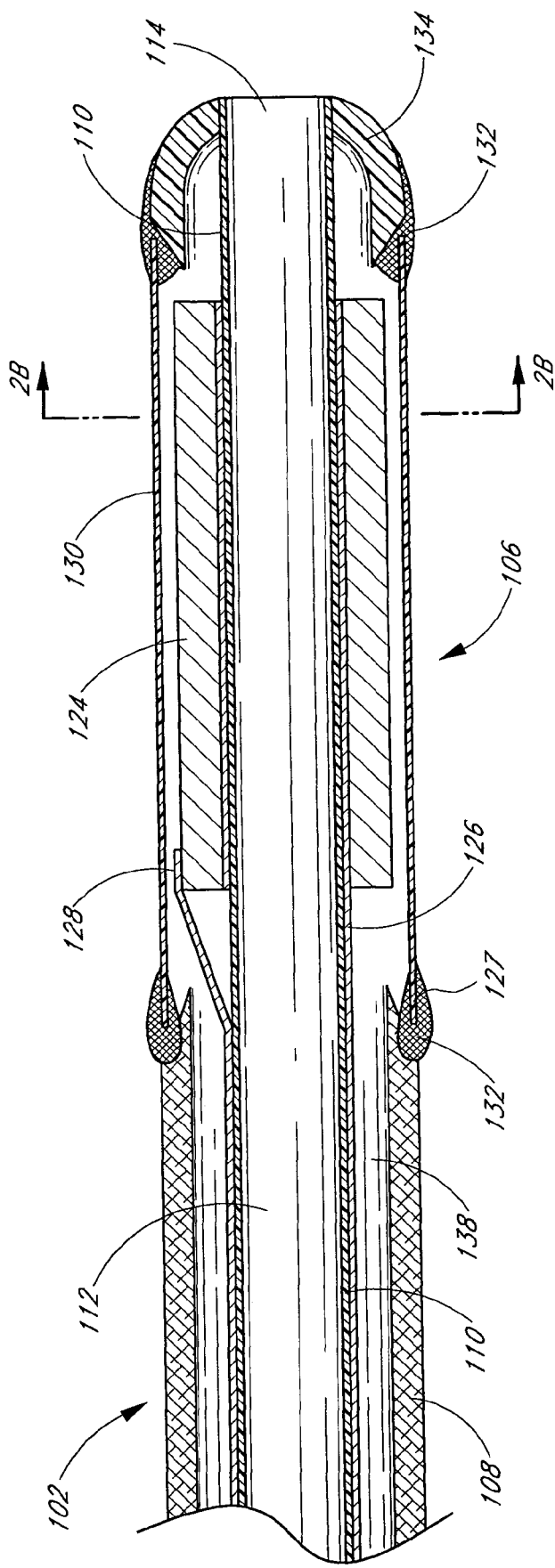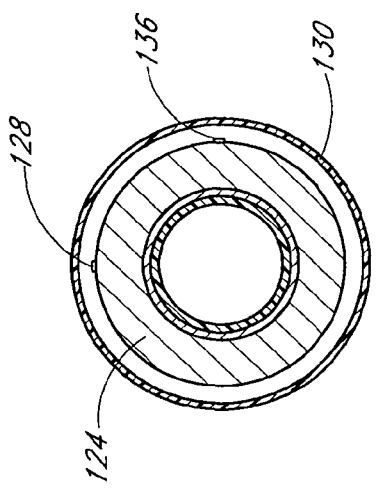
FIG.2A
FIG.2B

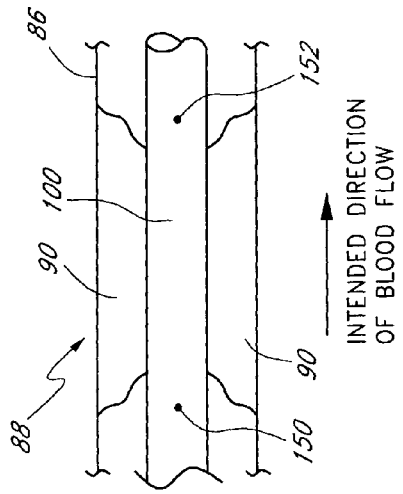
FIG. 7
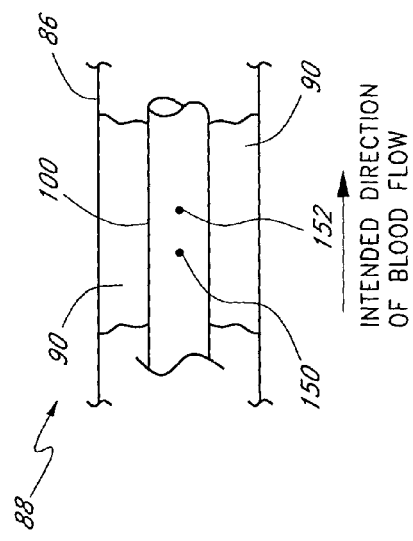
FIG. 8
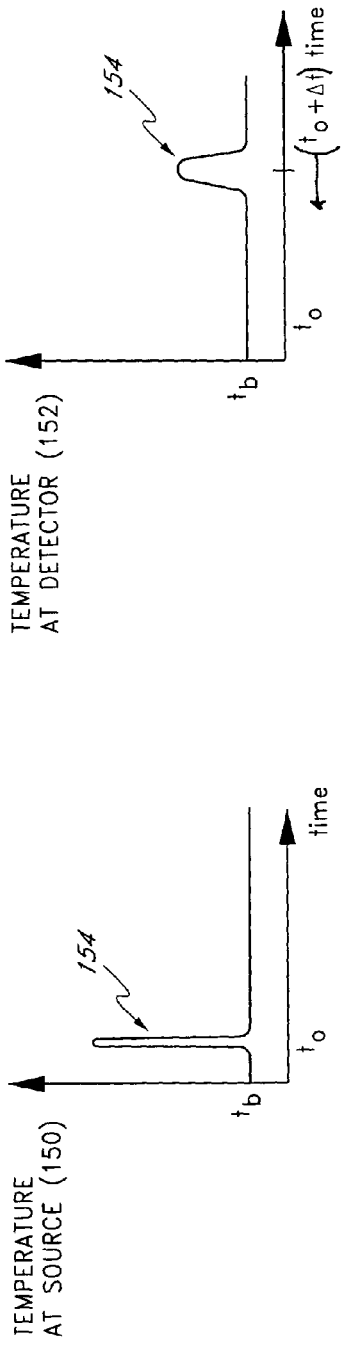
FIG. 9
FIG. 10

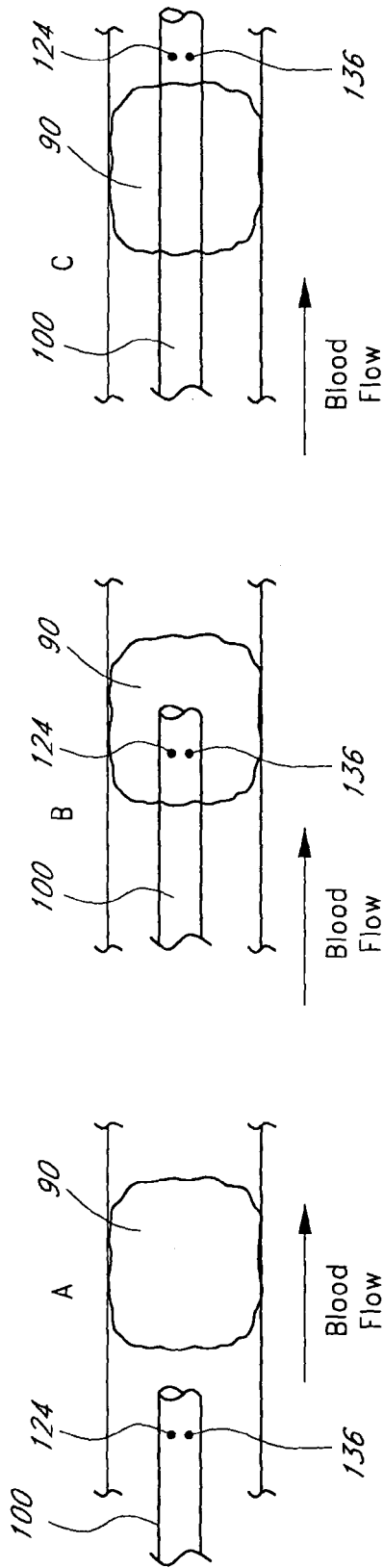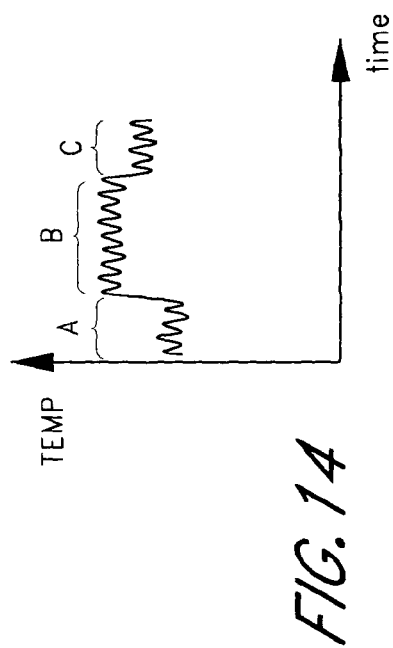

30 minutes

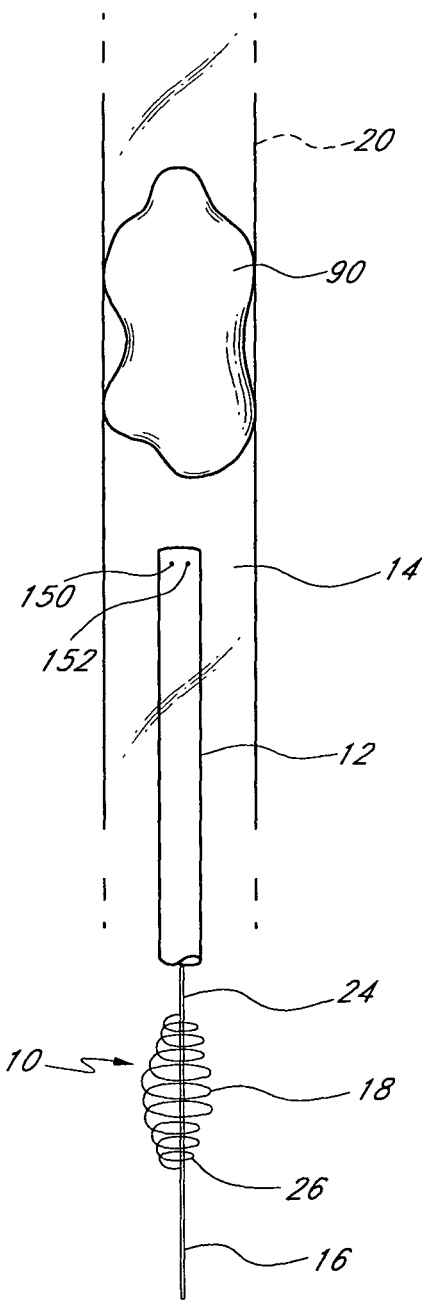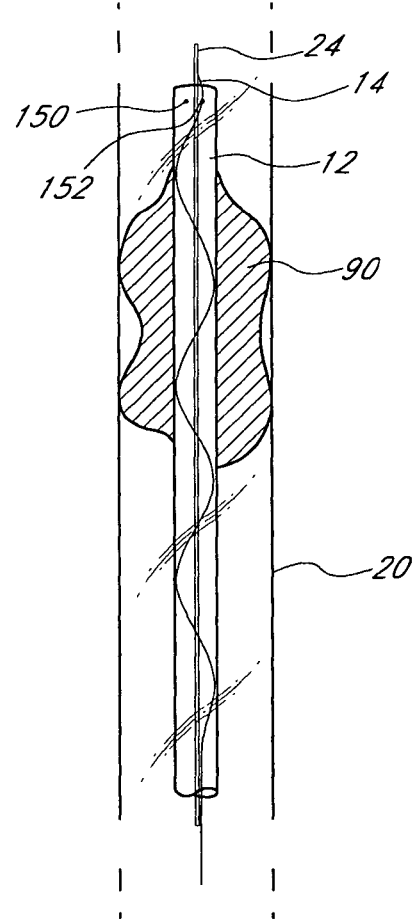
FIG. 17A
FIG. 17B

METHOD AND APPARATUS FOR DETECTING VASCULAR CONDITIONS WITH A CATHETER

PRIORITY APPLICATION

This application claims the benefit of U.S. Provisional Application 60/540,900 (filed 29 Jan. 2004), U.S. Provisional Application 60/540,703 (filed 30 Jan. 2004), and U.S. Provisional Application 60/583,301 (filed 25 Jun. 2004). These three priority applications are hereby incorporated by reference herein in their entirety.

FIELD OF THE INVENTION

The present invention relates in certain embodiments to medical devices and procedures, and more specifically to medical devices and procedures for detecting the conditions within a blood vessel.

BACKGROUND OF THE INVENTION

Human blood vessels occasionally become occluded by clots, plaque, thrombi, emboli or other substances that reduce the blood carrying capacity of the vessel. Cells that rely on blood passing through the occluded vessel for nourishment may die if the vessel remains occluded. This often results in grave consequences for a patient, particularly in the case of cells such as brain cells or heart cells.

Accordingly, several techniques are being developed for removing an occlusion from a blood vessel. Examples of such techniques include the introduction into the vasculature of therapeutic compounds—including enzymes—that dissolve blood clots. When such therapeutic compounds are introduced into the bloodstream, often systematic effects result, rather than local effects. Accordingly, recently catheters have been used to introduce therapeutic compounds at or near the occlusion. Mechanical techniques have also been used to remove an occlusion from a blood vessel. For example, ultrasonic catheters have been developed that include an ultrasound radiating member that is positioned in or near the occlusion. Ultrasonic energy is then used to ablate the occlusion. Other examples of mechanical devices include "clot grabbers" are "clot capture devices", as disclosed in U.S. Pat. Nos. 5,895,398 and 6,652,536, which are used to withdraw a blockage into a catheter. Other techniques involve the use of lasers and mechanical thrombectomy and/or clot macerator devices.

One particularly effective apparatus and method for removing an occlusion uses the combination of ultrasonic energy and a therapeutic compounds that removes an occlusion. Using such systems, a blockage is removed by advancing an ultrasound catheter through the patient's vasculature to deliver therapeutic compounds containing dissolution compounds directly to the blockage site. To enhance the therapeutic effects of the therapeutic compound, ultrasonic energy is emitted into the dissolution compound and/or the surrounding tissue. See, for example, U.S. Pat. No. 6,001,069.

SUMMARY OF THE INVENTION

In certain medical procedures, there are disadvantages associated with delivering excess therapeutic compound to the patient's vasculature. For example, certain therapeutic compounds, although effective in dissolving blockages in the vascular system, have adverse side effects on other biological systems. Additionally, certain therapeutic compounds are expensive, and therefore the cost of certain procedures can be reduced by avoiding delivery of excess therapeutic compound. Likewise, excess ultrasonic energy applied to patient's vasculature may have unwanted side effects. Thus, as a treatment progresses, the flow of therapeutic compound and/or the supply of ultrasonic energy to a treatment site can be reduced and eventually terminated. Conversely, if a clot dissolution treatment is progressing too slowly, the delivery of therapeutic compound and/or ultrasonic energy to the treatment site can be increased in an attempt to cause the treatment to progress faster. To date, it has been difficult to monitor the progression or efficacy of a clot dissolution treatment, and therefore to adjust the delivery of therapeutic compound and/or ultrasonic energy to the treatment site accordingly.

Therefore, an improved ultrasonic catheter capable of monitoring the progression or efficacy of a clot dissolution treatment has been developed. Using certain embodiments of this system, the delivery of therapeutic compound and/or the ultrasonic energy to the treatment site can be adjusted as the clot dissolution treatment progresses, eventually terminating the delivery of therapeutic compound and ultrasonic energy when the treatment has concluded.

Additionally, it is difficult to visualize the position of the occlusion in certain medical procedures. For example, it is particularly difficult to visualize occlusions in the distal anatomy, such as the neuro-vasculature. However, for many intravascular techniques, it is advantageous for the user to properly position the medical device, such as the catheter, with respect to the occlusion. Traditional techniques for positioning the medical device with respect to the occlusion typically involve positioning a radiopaque marker on the medical device, injecting a contrast medium into the blood vessel, and taking an angiogram. However, these techniques often do not provide necessary precision and/or rely on subjective visual inspections.

Therefore, improved methods and apparatuses have been developed for determining the position of the medical device with respect to the occlusion. These improved methods and apparatuses can be used in the distal anatomy—such as in the neuro-vasculature—and in combination with a method and apparatus to remove the occlusion.

Accordingly, in one embodiment of the present invention, a method for treating an occlusion comprises positioning a catheter at a treatment site in a patient's vasculature. A blockage is located at the treatment site. The method further comprises performing a medical treatment at the treatment site. The medical treatment is configured to reduce the blockage. The method further comprises making a plurality of temperature measurements at the treatment site while the medical treatment is being performed. The method further comprises using the temperature measurements to evaluate the reduction in the blockage.

In another embodiment of the present invention, a method of treating a patient comprises positioning a catheter at a treatment site in a patient's vasculature. A blockage is located at the treatment site. The method further comprises making a plurality of temperature measurements at the treatment site. The method further comprises using the temperature measurements to determine the position of the catheter with respect to the blockage. The method further comprises performing a medical treatment at the treatment site. The medical treatment is configured to reduce the blockage.

In one embodiment of the present invention, a method of treating a vascular obstruction located at a treatment site within a patient's vascular system comprises advancing a catheter to the treatment site. The method further comprises sensing a property at the treatment site. The method further comprises selecting a treatment parameter based, at least in part, upon the sensed property. The method further comprises treating the vascular obstruction.

In another embodiment of the present invention, a method comprises positioning a catheter within a patient's vasculature. The catheter includes a thermal source and a thermal detector. The method further comprises delivering thermal energy to the patient's vasculature from the thermal source. The method further comprises making a plurality of temperature measurements using the thermal detector. The method further comprises using the temperature measurements to determine the position of the catheter with respect to a blockage in the patient's vasculature.

In another embodiment of the present invention, a method of treating an obstruction within a patient's vasculature comprises positioning a catheter at a treatment site in the patient's vasculature. A blockage is located at the treatment site. The method further comprises performing a medical treatment at the treatment site. The medical treatment is configured to reduce the blockage. The method further comprises making a plurality of temperature measurements at the treatment site. The method further comprises using the temperature measurements to evaluate the reduction in the blockage.

In another embodiment of the present invention, a method of treating a vascular obstruction located at a treatment site within a patient's vascular system comprises advancing a catheter with a guidewire lumen over a guidewire to the treatment site. The method further comprises removing the guidewire from the guidewire lumen. The method further comprises advancing a sensor through the catheter guidewire lumen. The method further comprises sensing a condition of the treatment site with the sensor. The method further comprises treating the vascular obstruction.

In another embodiment of the present invention, a catheter for treating a vascular obstruction comprises an elongated tubular body configured to be inserted into a vascular system. The elongated tubular body has a distal end and a proximal end and defining a drug delivery lumen with at least one opening positioned at a treatment zone of the catheter. The catheter further comprises an optical sensor positioned at the treatment zone of the catheter. The catheter further comprises at least one fiber optic fiber extending from the optical sensor to the proximal end of the catheter.

In another embodiment of the present invention, a catheter for treating a vascular obstruction comprises an elongated tubular body configured to be inserted into a vascular system. The catheter further comprises a drug delivery lumen defined at least in part by the tubular body. The catheter further comprises a sensor element configured to be inserted into the tubular body and to extend from the distal end to the proximal end of the catheter. The sensor element comprises at least one fiber optic fiber and an optical sensor.

In another embodiment of the present invention, a catheter for treating a vascular obstruction comprises an elongated tubular body configured to be inserted into a vascular system. The elongated tubular body has a distal end and a proximal end and defines a drug delivery lumen with at least one opening positioned at a treatment zone of the catheter. The catheter further comprises an optical sensor positioned at the treatment zone of the catheter. The catheter further comprises at least one fiber optic fiber extending from the optical sensor to the proximal end of the catheter.

In another embodiment of the present invention, a system for treating a vascular obstruction within a patient's vascular system comprises an elongated tubular body configured to be inserted into the vascular system. The elongated tubular body has a distal end and a proximal end and defines a drug delivery lumen with at least one opening positioned at a treatment zone of the catheter. The system further comprises an ultrasound element positioned within the treatment zone. The system further comprises a sensor positioned at the treatment zone of the catheter. The system further comprises a display unit configured to display information based at least in part upon at least one fiber optic fiber extending from the optical sensor to the proximal end of the catheter.

BRIEF DESCRIPTION OF THE DRAWINGS

FIG. 2A is a cross-sectional view of a distal end of the ultrasound catheter of FIG. 1.

FIG. 2B is a cross-sectional view of the ultrasound catheter of FIG. 1 taken through line 2B-2B of FIG. 2A.

FIG. 7 is a schematic diagram illustrating an arrangement for using thermal measurements taken within a vascular occlusion for detecting reestablishment of blood flow.

FIG. 8 is a schematic diagram illustrating an arrangement for using thermal measurements taken outside a vascular occlusion for detecting reestablishment of blood flow.

FIG. 9 is an exemplary plot of temperature as a function of time at a thermal source.

FIG. 10 is an exemplary plot of temperature as a function of time at a thermal detector.

FIG. 11 is a schematic diagram of an ultrasound catheter positioned upstream of a vascular occlusion.

FIG. 12 is a schematic diagram of an ultrasound catheter positioned within a vascular occlusion.

FIG. 13 is a schematic diagram of an ultrasound catheter that has been passed through a vascular occlusion.

FIG. 14 is an exemplary plot of temperature measured by the ultrasound catheter as it is passed through the positions illustrated in FIGS. 11 through 13.

FIG. 17A is a schematic illustration of an occluded artery with a catheter including a thermal source, a temperature sensor, and a clot capture coil.

FIG. 17B is a schematic illustration of the clot capture coil of FIG. 17A passed through the catheter.

DETAILED DESCRIPTION OF PREFERRED EMBODIMENTS

Figure 1:
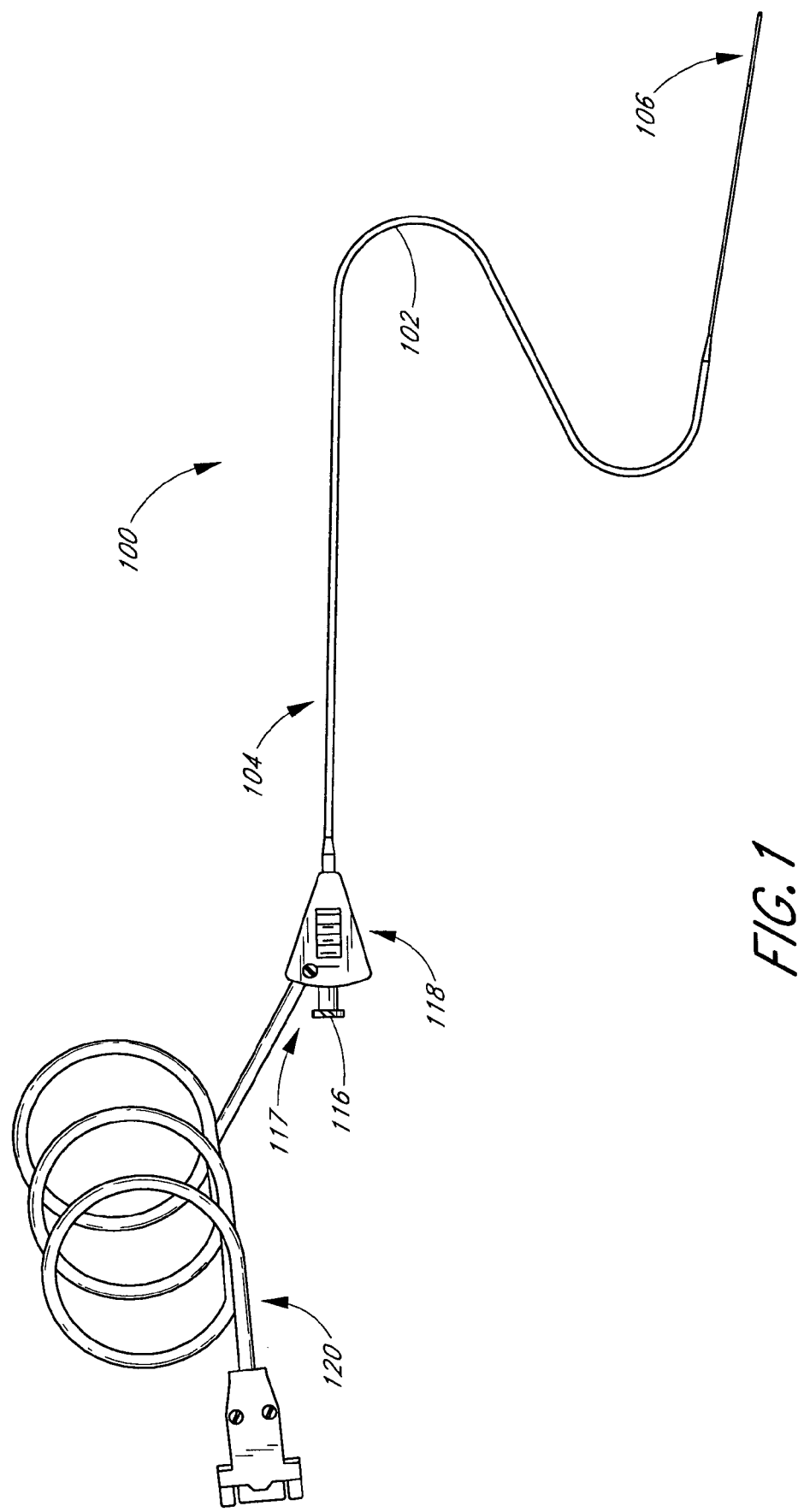
FIG. 1 is a side view of an ultrasound catheter that is particularly well suited for insertion into small blood vessels of the human body.

I. Introduction.

Certain embodiments described herein provide for a method and apparatus for sensing the condition at a treatment site within a patient's vascular system. The sensed condition may be used to guide or adjust treatment of the patient. In one embodiment, the treatment site is located at or near an obstruction within the patient's vascular system. In another embodiment, the obstruction is located within the patient's neurovascular system. As will be explained below, the condition may be used in a variety of ways to enhance treatment. For example, the sensed condition may be used to indicate the position of the obstruction relative to the treatment device, the degree to which blood flow has been reestablished and/or the condition of the patient. The sensed condition may determined from any of a number of measurable properties that provide useful information regarding the condition at the treatment site. Such properties include but are not limited to temperature, pressure, chemical and gas compositions within the vascular system at the treatment site.

As will be explained below, the method and apparatus for sensing the condition at the treatment site may be used in combination with a variety of therapeutic techniques. However, many of the preferred embodiments will be described in combination with an ultrasound catheter that is well suited for use in the treatment of small blood vessels or other body lumens having a small inner diameter. Such embodiments can be used to enhance the therapeutic effects of drugs, medication, pharmacological agents and other therapeutic compounds at a treatment site within the body. See, for example, U.S. Pat. Nos. 5,318,014; 5,362,309; 5,474,531; 5,628,728; 6,001,069; and 6,210,356. Certain embodiments described herein are particularly well suited for use in the treatment of thrombotic occlusions in small blood vessels, such as, for example, the cerebral arteries. However, such therapeutic compounds can also be used in wide variety of locations within the body, such as, for example, in other parts of the circulatory system, in solid tissues, in duct systems and in body cavities. The patents referenced above are hereby incorporated by reference herein.

It should be appreciated that the ultrasound catheters disclosed herein, and similar variations thereof, can also be used in applications wherein the ultrasonic energy provides a therapeutic effect by itself. For example, ultrasonic energy can be effective in preventing and/or reducing stenosis and/or restenosis; causing tissue ablation, abrasion or disruption; and promoting temporary or permanent physiological changes in intracellular or intercellular structures. Ultrasonic energy can also be used to agitate micro-balloons and/or microbubbles to cause a therapeutic compound to be delivered to a treatment site with greater efficiency. See, for example, U.S. Pat. Nos. 5,269,291 and 5,431,663, which are hereby incorporated by reference herein.

In still other embodiments, the method and apparatus for sensing the condition at a treatment site may be used in combination with therapeutic techniques and devices that do not use ultrasound energy. For example, the method and apparatus may be used in combination with a drug delivery catheter or a catheter configured to grab or otherwise remove an obstruction within the vessel.

As used herein, the terms "ultrasound energy" and "ultrasonic energy" are used broadly, and include their ordinary meanings, and further include mechanical energy transferred through pressure or compression waves with a frequency greater than about 20 kHz. In one embodiment, the waves of the ultrasonic energy have a frequency between about 500 kHz and about 20 MHz, and in another embodiment the waves of ultrasonic energy have a frequency between about 1 MHz and about 3 MHz. In yet another embodiment, the waves of ultrasonic energy have a frequency of about 3 MHz.

As used herein, the term "catheter" is used broadly, and includes its ordinary meaning, and further includes an elongate flexible tube configured to be inserted into the body of a patient, such as, for example, a body cavity, duct or vessel.

As used herein, the term "therapeutic compound" broadly refers, in addition to its ordinary meaning, to a drug, medicament, dissolution compound, genetic material, or any other substance capable of effecting physiological functions. Additionally, a mixture comprising such substances is encompassed within this definition of "therapeutic compound".

As used herein, the term "end" refers, in addition to its ordinary meaning, to a region, such that "proximal end" includes "proximal region", and "distal end" includes "distal region".

As used herein, the term "proximal element joint" refers generally, and in addition to its ordinary meaning, to a region where a proximal portion of an ultrasound radiating member is attached to other components of an ultrasound catheter.

As used herein, the term "treatment site" refers generally, and in addition to its ordinary meaning, to a region where a medical procedure is performed within a patient's body. Where the medical procedure is a treatment configured to reduce an occlusion within the patient's vasculature, the term "treatment site" refers to the region of the obstruction, as well as the region upstream of the obstruction and the region downstream of the obstruction.

II. Exemplary Embodiments of an Ultrasound Catheter.

FIGS. 1 through 2B illustrate an exemplary embodiment of an ultrasound catheter 100 that is well suited for use within small vessels of the distal anatomy, such as the remote, small diameter blood vessels located in the brain.

As shown in FIGS. 1 and 2A, the ultrasound catheter 100 generally comprises a multi-component tubular body 102 having a proximal end 104 and a distal end 106. The tubular body 102 and other components of the catheter 100 can be manufactured in accordance with any of a variety of techniques well known in the catheter manufacturing field. As discussed in more detail below, suitable materials and dimensions can be readily selected taking into account the natural and anatomical dimensions of the treatment site and of the desired percutaneous access site.

The tubular body 102 can be divided into multiple sections of varying stiffness. For example, a first section, which includes the proximal end 104, is generally more stiff than a second section, which lies between the proximal end 104 and the distal end 106 of the tubular body 102. This arrangement facilitates the movement and placement of the ultrasound catheter 100 within small vessels. A third section, which includes at least one ultrasound radiating member 124, is generally stiffer than the second section due to the presence of the ultrasound radiating member 124.

In the exemplary embodiments described herein, the assembled ultrasound catheter has sufficient structural integrity, or "pushability," to permit the catheter to be advanced through a patient's vasculature to a treatment site without significant buckling or kinking. In addition, in certain embodiments, the catheter can transmit torque (that is, the catheter has "torqueability"), thereby allowing the distal portion of the catheter to be rotated into a desired orientation by applying a torque to the proximal end.

Referring now to FIG. 2A, the elongate flexible tubular body 102 comprises an outer sheath 108 positioned upon an inner core 110. In an embodiment particularly well suited for small vessels, the outer sheath 108 comprises a material such as extruded PEBAX®, polytetrafluoroethylene ("PTFE"), polyetheretherketone ("PEEK"), polyethylene ("PE"), polyimides, braided and/or coiled polyimides and/or other similar materials. The distal end portion of the outer sheath 108 is adapted for advancement through vessels having a small diameter, such as found in the brain. In an exemplary embodiment, the distal end portion of the outer sheath 108 has an outer diameter between about 2 French and about 5 French. In another exemplary embodiment, the distal end portion of the outer sheath 108 has an outer diameter of about 2.8 French. In an exemplary embodiment, the outer sheath 108 has an axial length of approximately 150 centimeters. In other embodiments, other dimensions can be used.

In other embodiments, the outer sheath 108 can be formed from a braided and/or coiled tubing comprising, for example, high or low density polyethylenes, urethanes, nylons, and so forth. Such a configuration enhances the flexibility of the tubular body 102. For enhanced pushability and torqueability, the outer sheath 108 can be formed with a variable stiffness from the proximal to the distal end. To achieve this, a stiffening member can be included along the proximal end of the tubular body 102. In one exemplary embodiment, the pushability and flexibility of the tubular body 102 are controlled by manipulating the material and thickness of the tubular body 102, while the torqueability, kink resistance, distortion (also referred to as "ovalization") and burst strength of the tubular body 102 are controlled by incorporation of braiding and/or coiling along or into the tubular body 102.

The inner core 110 at least partially defines a delivery lumen 112. In an exemplary embodiment, the delivery lumen 112 extends longitudinally along substantially the entire length of the ultrasound catheter 100. The delivery lumen 112 comprises a distal exit port 114 and a proximal access port 116. Referring again to FIG. 1, the proximal access port 116 is defined by therapeutic compound inlet port 117 of backend hub 118, which is attached to the proximal end 104 of the tubular body 102. In an exemplary embodiment, the illustrated backend hub 118 is attached to a control box connector 120, which will be described in more detail below. In a modified embodiment, electronics and/or control circuitry for controlling the ultrasound radiating member are incorporated into the backend hub 118.

In an exemplary embodiment, the delivery lumen 112 is configured to receive a guide wire (not shown). In one embodiment, the guidewire has a diameter of approximately 0.008 inches to approximately 0.020 inches. In another embodiment, the guidewire has a diameter of about 0.014 inches. In an exemplary embodiment, the inner core 110 comprises polyimide or a similar material which, in some embodiments, can be braided and/or coiled to increase the flexibility of the tubular body 102.

Referring now to the exemplary embodiment illustrated in FIGS. 2A and 2B, the distal end 106 of the tubular body 102 includes an ultrasound radiating member 124. In an exemplary embodiment, the ultrasound radiating member 124 comprises an ultrasound transducer that converts, for example, electrical energy into ultrasonic energy. In a modified embodiment, the ultrasonic energy can be generated by an ultrasound transducer that is remote from the ultrasound radiating member 124, and the ultrasonic energy can be transmitted via, for example, a wire to the ultrasound radiating member 124.

As illustrated in FIGS. 2A and 2B, the ultrasound radiating member 124 is configured as a hollow cylinder. As such, the inner core 110 extends through the hollow core of the ultrasound radiating member 124. In an exemplary embodiment, the ultrasound radiating member 124 is secured to the inner core 110 in a suitable manner, such as with an adhesive. A potting material can also be used to help secure the ultrasound radiating member 124 to the inner core 110.

In other embodiments, the ultrasound radiating member 124 has a different shape. For example, the ultrasound radiating member 124 can be shaped as a solid rod, a disk, a solid rectangle or a thin block. In still other embodiments, the ultrasound radiating member 124 comprises a plurality of smaller ultrasound radiating elements. The embodiments illustrated in FIGS. 1 through 2B advantageously provide enhanced cooling of the ultrasound radiating member 124. For example, in an exemplary embodiment, a therapeutic compound is delivered through the delivery lumen 112. As the therapeutic compound passes through the central core of the ultrasound radiating member 124, the therapeutic compound advantageously removes heat generated by the ultrasound radiating member 124. In another embodiment, a return path can be formed in region 138 between the outer sheath 108 and the inner core 110 such that coolant from a coolant system passes through region 138.

In an exemplary embodiment, the ultrasound radiating member 124 is selected to produce ultrasonic energy in a frequency range adapted for a particular application. Suitable frequencies of ultrasonic energy for the applications described herein include, but are not limited to, from about 20 kHz to about 20 MHz. In one embodiment, the frequency is between about 500 kHz and about 20 MHz, and in another embodiment, the frequency is between about 1 MHz and about 3 MHz. In yet another embodiment, the ultrasonic energy has a frequency of about 3 MHz. In one embodiment, the dimensions of the ultrasound radiating member 124 are selected to allow the germination of sufficient acoustic energy to enhance lysis without significantly adversely affecting catheter maneuverability.

As described above, in the embodiment illustrated in FIGS. 1 through 2B, ultrasonic energy is generated from electrical power supplied to the ultrasound radiating member 124. The electrical power can be supplied through control box connector 120, which is connected to conductive wires 126, 128 that extend through the tubular body 102. In another embodiment, the electrical power can be supplied from a power supply contained within the backend hub 118. In such embodiments, the conductive wires 126, 128 can be secured to the inner core 110, can lay along the inner core 110, and/or can extend freely in the region 138 between the inner core 110 and the outer sheath 108. In the illustrated embodiments, the first wire 126 is connected to the hollow center of the ultrasound radiating member 124, while the second wire 128 is connected to the outer periphery of the ultrasound radiating member 124. In an exemplary embodiment, the ultrasound radiating member 124 comprises a transducer formed of a piezoelectric ceramic oscillator or a similar material.

In the exemplary embodiment illustrated in FIGS. 2A and 2B, the distal end 106 of the tubular body 102 includes a sleeve 130 that is generally positioned about the ultrasound radiating member 124. In such embodiments, the sleeve 130 comprises a material that readily transmits ultrasonic energy. Suitable materials for the sleeve 130 include, but are not limited to, polyolefins, polyimides, polyesters and other materials that readily transmit ultrasonic energy with minimal energy absorption. In an exemplary embodiment, the proximal end of the sleeve 130 is attached to the outer sheath 108 with an adhesive 132. In certain embodiments, to improve the bonding of the adhesive 132 to the outer sheath 108, a shoulder 127 or notch is formed in the outer sheath 108 for attachment of the adhesive 132 thereto. In an exemplary embodiment, the outer sheath 108 and the sleeve 130 have substantially the same outer diameter. In other embodiments, the sleeve 130 can be attached to the outer sheath 108 using heat bonding techniques, such as radiofrequency welding, hot air bonding, or direct contact heat bonding. In still other embodiments, techniques such as over molding, dip coating, film casting and so forth can be used.

Still referring to the exemplary embodiment illustrated in FIGS. 2A and 2B, the distal end of the sleeve 130 is attached to a tip 134. As illustrated, the tip 134 is also attached to the distal end of the inner core 110. In one embodiment, the tip is between about 0.5 millimeters and about 4.0 millimeters long. In another embodiment, the tip is about 2.0 millimeters long. As illustrated, in certain embodiments the tip is rounded in shape to reduce trauma or damage to tissue along the inner wall of a blood vessel or other body structure during advancement toward a treatment site.

As illustrated in FIG. 2B, the ultrasound catheter 100 can include at least one temperature sensor 136 in the distal region of the catheter. In one embodiment, the temperature sensor 136 is positioned on or near the ultrasound radiating member 124. Suitable temperature sensors include but are not limited to, diodes, thermistors, thermocouples, resistance temperature detectors, and fiber optic temperature sensors that use thermalchromic liquid crystals. In an exemplary embodiment, the temperature sensor 136 is operatively connected to a control box (not shown) through a control wire that extends along the tubular body 102 and through the backend hub 118, and that is operatively connected to the control box via control box connector 120. In an exemplary embodiment, the control box includes a feedback control system having the ability to monitor and control the power, voltage, current and phase supplied to the ultrasound radiating member 124. In this manner, the temperature along a selected region of the ultrasound catheter 100 can be monitored and controlled. Details of the control box can be found in U.S. Patent Application Publications 2004/0024347 and 2004/0049148, which are both incorporated by reference herein in their entirety.

In embodiments wherein multiple ultrasound radiating members are positioned in the catheter distal region, a plurality of temperature sensors can be positioned adjacent to the ultrasound radiating members. For example, in one such embodiment, a temperature sensor is positioned on or near each of the multiple ultrasound radiating members.

In an exemplary application, the ultrasound catheter 100 can be used to remove an occlusion from a small blood vessel. In such an exemplary application, a free end of a guidewire is percutaneously inserted into a patient's vasculature at a suitable first puncture site. The guidewire is advanced through the vasculature toward a treatment site where the blood vessel is occluded by a thrombus. In one embodiment, the guidewire is directed through the thrombus. In another embodiment, the guidewire is directed through the thrombus, and is left in the thrombus during treatment to aid in dispersion of the therapeutic compound into the thrombus.

After advancing the guidewire to the treatment site, the ultrasound catheter 100 is percutaneously inserted into the patient's vasculature through the first puncture site, and is advanced along the guidewire towards the treatment site using conventional over-the-guidewire techniques. The ultrasound catheter 100 is advanced until the distal end is positioned at or within the occlusion. In a modified embodiment, the catheter distal end includes one or more radiopaque markers (not shown) to aid in positioning the catheter distal end at the treatment site.

After the ultrasound catheter 100 is positioned, the guidewire can be withdrawn from the delivery lumen 112. A therapeutic compound source (not shown), such as a syringe with a Luer fitting, is hydraulically connected to the therapeutic compound inlet port 117, and the control box connector 120 is connected to the control box. This configuration allows a therapeutic compound to be delivered through the delivery lumen 112 and the distal exit port 114 to the occlusion. One exemplary therapeutic compound appropriate for treating a thrombus is an aqueous solution containing heparin, urokinase, streptokinase, and/or tissue plasminogen activator.

The ultrasound radiating member 124 can be activated to emit ultrasonic energy from the distal region of the ultrasound catheter 100. As described above, suitable frequencies for the ultrasonic energy include, but are not limited to, from about 20 kHz to about 20 MHz. In one embodiment, the frequency is between about 500 kHz and about 20 MHz, and in another embodiment the frequency is between about 1 MHz and 3 MHz. In yet another embodiment, the ultrasonic energy has a frequency of about 3 MHz. In an exemplary embodiment, the therapeutic compound and ultrasonic energy are applied until the thrombus is partially or entirely dissolved. Once the thrombus has been dissolved sufficiently, the ultrasound catheter 100 is withdrawn from the treatment site.

Methods of Manufacture.

The catheters described herein can be manufactured by sequentially positioning the various catheter components onto the catheter assembly. For example, in one method of manufacture, the ultrasound radiating member 124 is positioned over the outer surface of an intermediate portion of an elongate tube. The elongate tube serves as the inner core 110 and defines the delivery lumen 112. The first and second wires 126, 128 are then also disposed along the outer surface of the inner core 110 proximal to the ultrasound radiating member 124. The first wire 126 is electrically connected to an inner surface of the ultrasound radiating member 124, and the second wire is electrically connected to an outer surface of the ultrasound radiating member 124, as illustrated in FIG. 2A. The electrical connections can be accomplished using, for example, a solder joint.

After the ultrasound radiating member 124 and wires 126, 128 are secured to the inner core 110, an outer sheath 108 is positioned over a portion of the inner core, leaving the ultrasound radiating member 124 uncovered by the outer sheath 108, as illustrated in FIG. 2A. A cylindrical sleeve 130 is then positioned over the ultrasound radiating member 124, and is secured to the distal end of the outer sheath 108 with an adhesive 132. A rounded distal tip 134 is then secured to the sleeve 130 and the inner core 110, and any excess length of the elongate tube extending distal to the distal tip 134 is removed.

Although an exemplary catheter manufacturing technique has been expounded above, other manufacturing techniques can be used, additional components can be included, and the components set forth above can be modified. For example, in certain embodiments, the ultrasound catheter 100 further comprises a temperature sensor 136 positioned near the ultrasound radiating member 124, as described above. In other embodiments, the outer sheath 108 can be modified to manipulate the flexibility of the catheter 100, such as by including a stiffening component or metallic braiding and/or coiling.

Delivery Lumen with Coil Composite Tubing.

As described above, if the ultrasound catheter buckles or kinks during advancement through the patient's vasculature, it may not be possible to deliver the ultrasound radiating member to the treatment site. Furthermore, buckling or kinking of the catheter can damage the patient's vasculature, and can cause binding of the guidewire within the tubular body. Thus, improved ultrasound catheters have been developed that have enhanced resistance to kinking and buckling, while retaining sufficient flexibility to enable navigation through difficult regions of the patient's vasculature. These enhanced properties can be obtained by providing an improved composite delivery lumen.

Figure 3A:
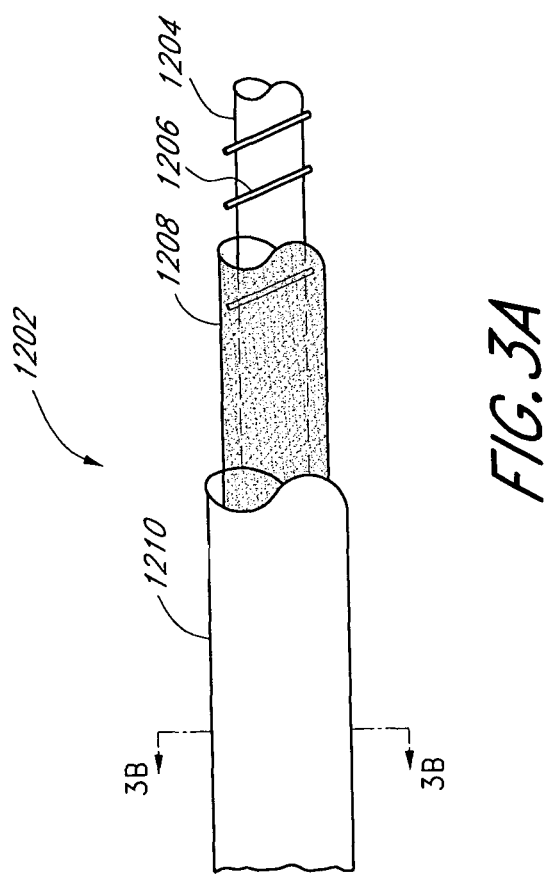
FIG. 3A is a partial cutaway side view of a composite tubular body with improved flexibility and kink- and buckle-resistance.
Figure 3B:
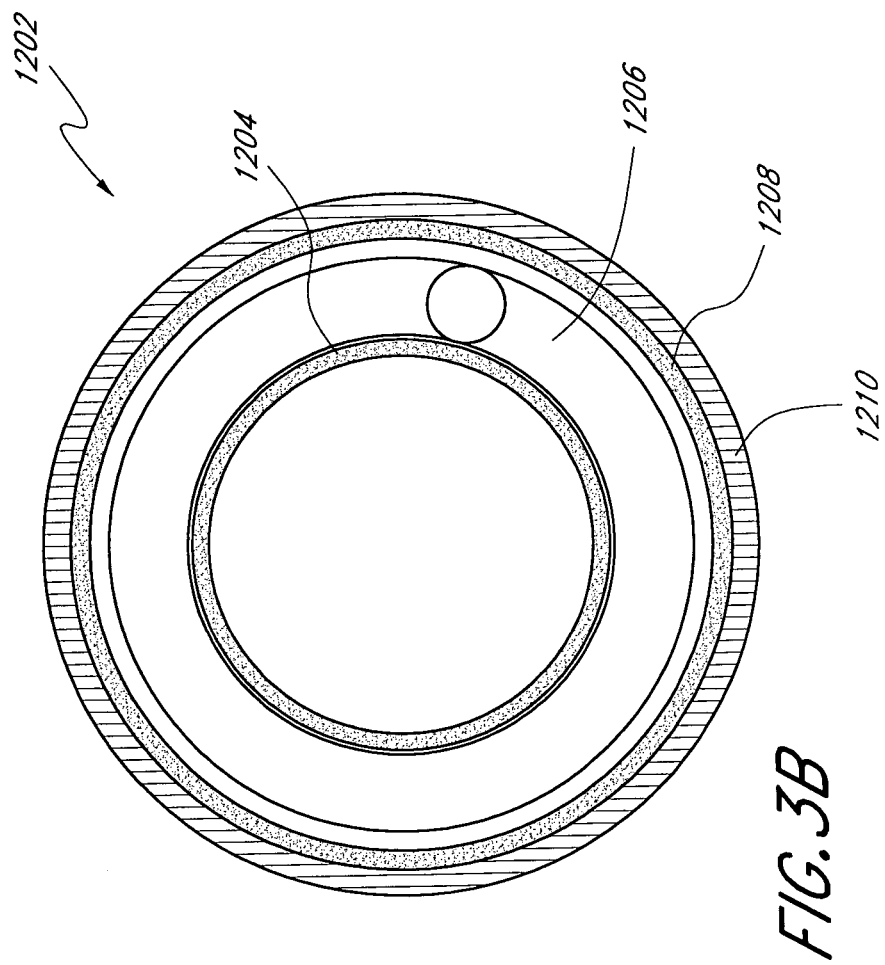
FIG. 3B is a cross-sectional view of the catheter of FIG. 3A taken along line 3B-3B.

FIGS. 3A and 3B illustrate an exemplary composite delivery lumen 1202 that can be used in an improved ultrasound catheter. As illustrated in this exemplary embodiment, the delivery lumen 1202 has a composite construction that includes an Teflon® internal liner 1204 surrounded by a stainless steel coil 1206, which is overlaid with an outer cover. In the exemplary embodiment illustrated in FIGS. 3A and 3B, the outer cover is a composite cover comprising a PEBAX® inner wall 1208 and a TECOFLEX® outer skin 1210. Other materials can be used in other embodiments. The inner diameter of the internal liner 1204 is generally configured to allow free movement of a standard guidewire therethrough. For example, in one exemplary embodiment, the inner diameter of the internal liner 1204 is approximately 0.018 inches±0.005 inches. In other embodiments, the inner diameter of the internal liner 1204 is approximately 0.018 inches±0.010 inches. In still other embodiments, the inner diameter of the internal liner 1204 is approximately 0.018 inches±0.100 inches.

In embodiments wherein the ultrasound catheter includes the composite delivery lumen 1202 described herein, the kink resistance and flexibility of the catheter 100 is advantageously increased, as compared to a catheter with a delivery lumen consisting solely of polyimide. This configuration also reduces the tendency of the tubular body to become ovular when passed through difficult regions of the patient's vasculature, thereby reducing the likelihood of binding of the guidewire within the composite delivery lumen 1202. Additionally, the presence of the stainless steel coil 1206 increases the burst strength, kink resistance and flexibility of the composite delivery lumen 1202, and provides for a stronger bond at locations where other catheter components are to be bonded to the composite delivery lumen 1202—such as at the distal and proximal ends of the composite delivery lumen 1202.

In certain embodiments, the delivery lumen is configured with dimensions to increase the size of the region 138 (see FIG. 2A) between the delivery lumen and the outer sheath. Providing a larger region 138 allows more room for electrical conductors, such as the conductors configured to provide power to an ultrasound radiating member and a temperature sensor provided in the catheter.

The techniques for increasing the maneuverability of the ultrasound catheter described herein can be applied to the entire length of the tubular body, or can be applied to a portion of the tubular body. In other embodiments, the techniques can be applied along different lengths of the catheter to varying degrees. For example, in one such embodiment, the tubular body can be configured with a varying flexibility, such that the flexibility of the tubular body gradually increases from the proximal region to the distal region. Other characteristics of the tubular body, such as kink resistance and torqueability, can be can be varied along the length of the catheter.

In embodiments wherein the delivery lumen comprises a composite delivery lumen 1202 as described above, and as illustrated in FIGS. 3A and 3B, a polyimide sleeve can be incorporated into the backend hub 118 (see FIG. 1) to facilitate mating of the composite delivery lumen 1202 with the backend hub 118. For example, FIG. 4 illustrates selected internal components of the backend hub 118 that can be used in connection with the composite delivery lumen 1202.

Figure 4:
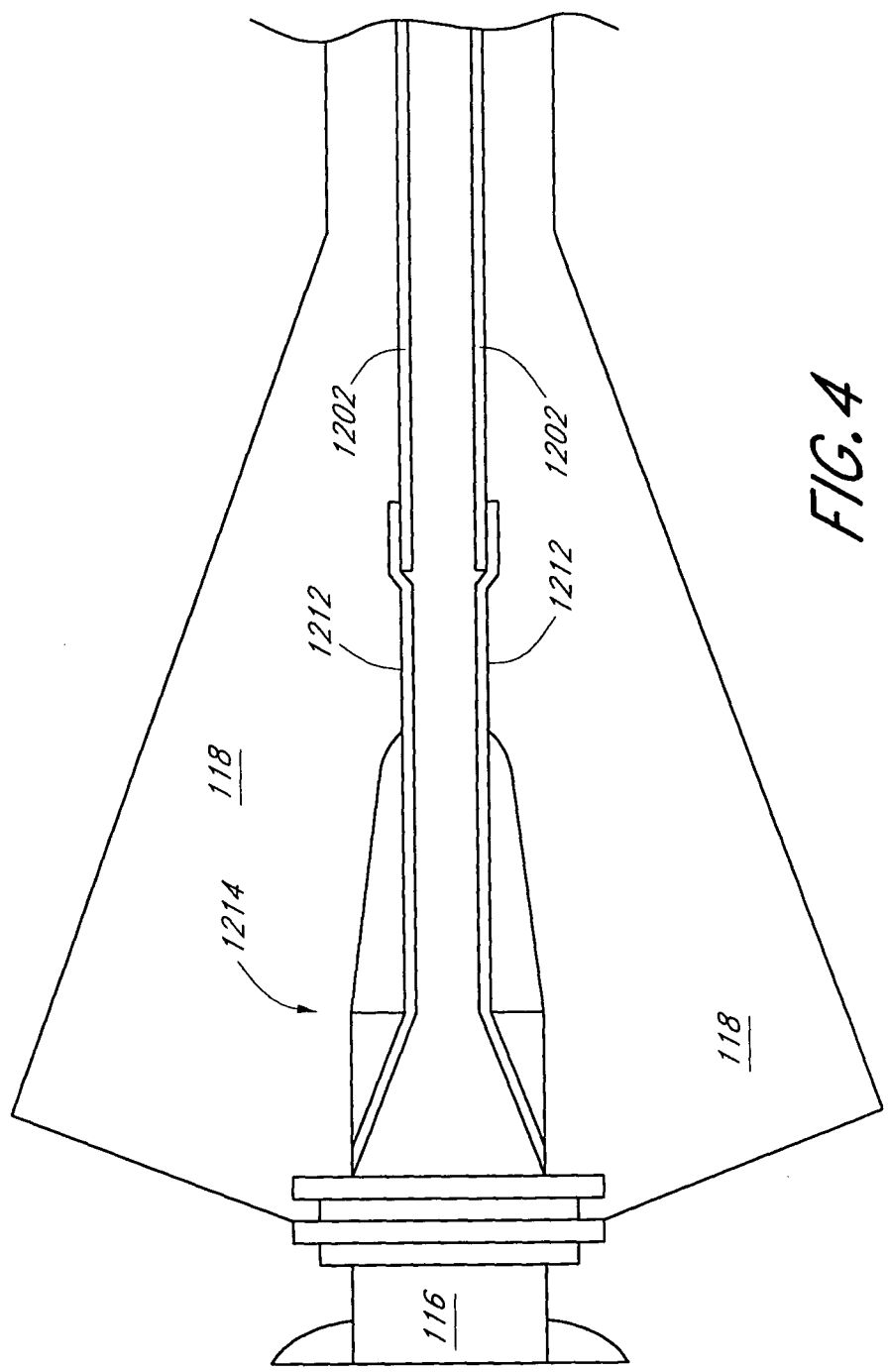
FIG. 4 is a cutaway view of selected internal components of a backend hub configured for use with the composite tubular body of FIGS. 3A and 3B.

For example, the backend hub 118 illustrated in FIG. 4 includes a polyimide sleeve 1212 that is bonded to the proximal end of the composite delivery lumen 1202. In an exemplary embodiment, the polyimide sleeve 1212 has an inner diameter substantially equal to the inner diameter of the composite delivery lumen 1202. One end of the polyimide sleeve 1212 can be expanded over the composite delivery lumen 1202 to create a secure slip-fit joint with a relatively smooth transition along the inner diameter. Heat and/or adhesives can be used to bond and seal the joint. This configuration advantageously facilitates passage of a guidewire through the backend hub 118 and into the composite delivery lumen 1202. Additionally, this configuration advantageously reduces (a) exposure of the composite delivery lumen 1202 to ultraviolet light during curing operations, and (b) the amount of bending stress that the joint between the polyimide sleeve 1212 and composite delivery lumen 1202 is subjected to during assembly. In one embodiment, the length of the joint between the polyimide sleeve 1212 and the composite delivery lumen 1202 is approximately equal to the length of the proximal element joint, as defined above.

The other end of the polyimide sleeve 1212 is engaged with a Luer fitting 1214 in the backend hub 118 to anchor the polyimide sleeve 1212 in place. In an exemplary embodiment, the length of engagement between the polyimide sleeve 1212 and the Luer fitting 1214 is approximately 0.400 inches, although other dimensions can be used in other embodiments.

Figure 5:
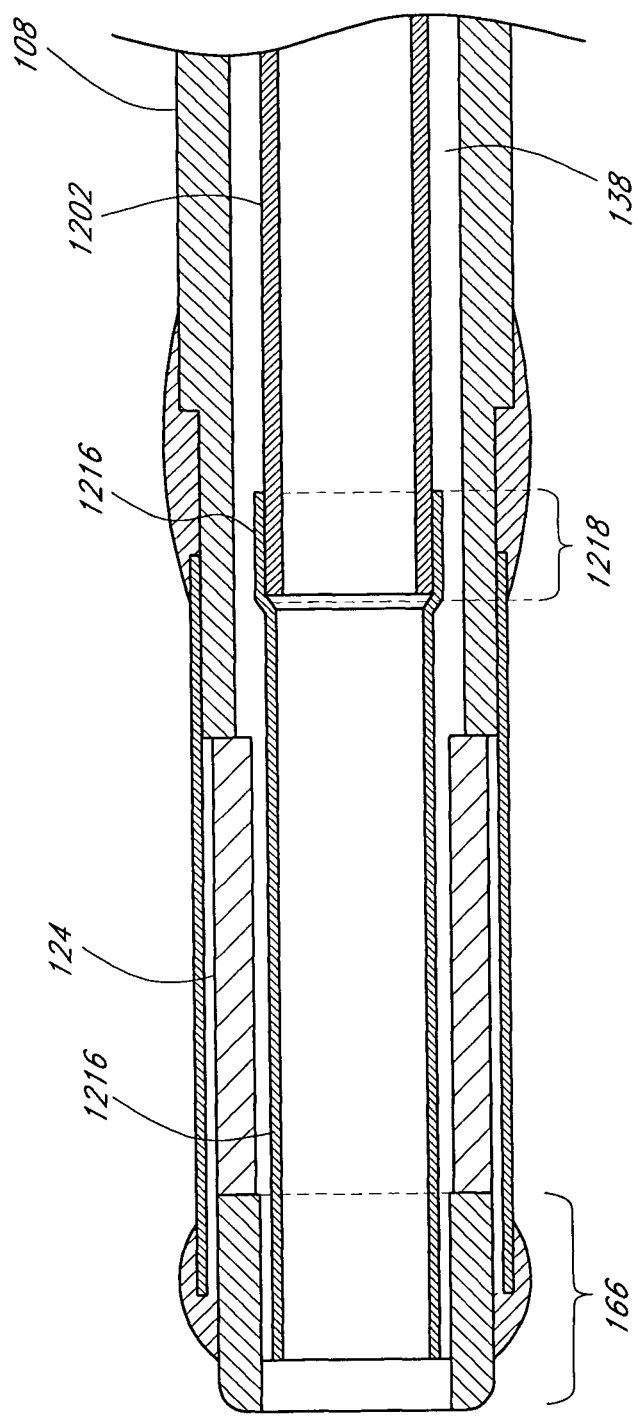
FIG. 5 is a cross-sectional view of the distal end of an ultrasound catheter that includes the composite tubular body of FIGS. 3A and 3B.

In an exemplary embodiment wherein the delivery lumen comprises a composite delivery lumen 1202, a polyimide tube 1216 is bonded to the distal end of the composite delivery lumen 1202, as illustrated in FIG. 5. The polyimide tube 1216 serves as a delivery lumen through the region of the ultrasound radiating member 124. The bond between the distal end of the composite delivery lumen 1202 and the polyimide tube 1216, referred to herein as the "distal delivery lumen bond" 1218, is located within the outer sheath 108 in an exemplary embodiment. In an such embodiments, the distal delivery lumen bond 1218 has a length between approximately 0.020 inches and approximately 0.025 inches. In another embodiment, the distal delivery lumen bond 1218 has a length between approximately 0.010 inches and approximately 0.035 inches. Other dimensions can be used in other embodiments. For example, in one embodiment, the distal delivery lumen bond 1218 has the minimum length permissible while still providing sufficient strength to hold the composite delivery lumen 1202 and the polyimide tube 1216 together.

Still referring to the exemplary embodiment illustrated in FIG. 5, the polyimide tube 1216 passes through the inner diameter of the ultrasound radiating member 124. In one such embodiment, the polyimide tube 1216 has an inner diameter of approximately 0.023 inches at the distal delivery lumen bond (where it fits over the composite delivery lumen 1202), and has an inner diameter of approximately 0.018 inches within the ultrasound radiating member 124. In such embodiments, the length of the polyimide tube 1216, including the length of the distal delivery lumen bond 1218, is between about 0.151 inches and about 0.182 inches. Other dimensions for the polyimide tube 1216 can be used in other embodiments.

The configuration of the distal delivery lumen bond 1218 described herein advantageously provides a secure, slip-fit joint between the composite delivery lumen 1202 and the polyimide tube 1216. The distal delivery lumen bond 1218 has a relatively smooth transition along the inner diameter. Heat can be used to bond and seal the joint. No adhesive is necessary, although an adhesive can be used in a modified embodiment. Using heat to bond the joint advantageously provides a high bond strength, allows close control of any reflow of the delivery lumen inner diameter, and provides a relatively small, low profile bond. However, other bonding techniques can be used in other embodiments.

The distal delivery lumen bond 1218 configuration described herein advantageously facilitates passage of a guidewire therethrough, and generally improves the flexibility of the proximal element joint. This configuration enhances catheter accessibility to the distal vasculature. This configuration also covers sharp ends which can be present at the distal end of the composite delivery lumen 1202, such as from the coil 1206.

Furthermore, the presence of the distal delivery lumen bond 1218 in region 138 between the composite delivery lumen 1202 and the outer sheath 108 creates a narrow passage which can be used to hold electrical conductors in place, such as the wires 126, 128 used to drive an ultrasound radiating member 124 or to transmit signals to and from a temperature sensor 136. This configuration can also reduce the likelihood of accidental disconnection of the wire 126, 128 from the ultrasound radiating member 124. In a modified embodiment, the ultrasound radiating member 124 is etched in the region of the distal delivery lumen bond 1218. The etching generally increases the strength of the distal delivery lumen bond 1218.

Ultrasound Catheter with Reduced Distal Rigid Section.

As described previously, an ultrasound catheter often has a region of decreased flexibility in the distal region near the ultrasound radiating member. This distal rigid section can impede passage of the catheter through difficult regions of the patient's vasculature, especially as the length of the distal rigid section increases. This difficulty is often manifested when the flexible distal tip becomes ovular and pinches the guidewire during tracking of the ultrasound catheter over the guidewire.

The ability of the ultrasound catheter to reliably track the guidewire can be improved by decreasing the length of the distal tip region 166, which is defined as the length of catheter extending beyond the ultrasound radiating member. For example, in one embodiment of an ultrasound catheter with improved guidewire tracking performance, the length of the distal tip region 166 is between approximately 0.35 inches and approximately 0.45 inches. Indeed, implementation of design improvements such as this allow the length of the ultrasound radiating member 124 to be increased—thereby advantageously allowing more ultrasonic energy to be delivered to the treatment site—without adversely affecting the ability of the ultrasound catheter to reliably track the guidewire in distal regions of the patient's vasculature. Furthermore, decreasing the length of the distal tip region 166 advantageously reduces the tendency of the distal exit port 114 to become ovular and bind on the guidewire (commonly referred to as "fishmouthing") as the catheter is passed through the patient's vasculature.

Other aspects of the ultrasound catheter distal tip design can be manipulated to reduce the length of the distal rigid region 166, and therefore to enhance the maneuverability of the ultrasound catheter. For example, the ability of the ultrasound catheter to reliably track the guidewire can be improved by reducing the wicking of adhesive 132 (see FIG. 2A) in the region of the proximal element joint. This can be accomplished by using less adhesive 132 in the proximal element joint, and/or by modifying the bonding methods and techniques at the proximal element joint, as described herein. The strength of the proximal element joint can be maintained with less adhesive by increasing the "overlap" between the sleeve 130 and the outer sheath 108.

Ultrasound catheters manufactured according to the various techniques provided herein have advantageous physical properties that facilitate delivery of the catheter to a treatment site located within a patient's distal vasculature. The mechanical properties of these catheters, such as stiffness, guidewire movement, and other properties, can be tested using standard testing equipment, such as tensile testers, force gauges, and stiffness testers available from Tinius Olsen (Horsham, Pa.). Catheter designs can be evaluated in a water bath at approximately 37° C. to simulate conditions encountered within a patient's vasculature.

For example, the stiffness of the catheter as a function of axial catheter position can be determined using an INSTRON® tensile strength testing machine. In one exemplary embodiment, the stiffness of the catheter is less than about 0.05 pounds in a region within about 20 cm from the distal catheter tip. In another exemplary embodiment, the stiffness of the catheter is less than about 0.15 pounds in a region within about 20 cm from the distal tip. In another exemplary embodiment, the stiffness of the catheter is less than about 0.10 pounds in a region within about 30 cm from the distal tip. In another exemplary embodiment, the stiffness of the catheter is less than about 0.20 pounds in a region within about 30 cm from the distal tip.

Guidewire movement, which can be hindered by kinking or distortion (also referred to as "ovalization") of the tubular body, can be determined by observing guidewire movement through loops and/or curves of varying diameter. For example, in one test, a standard 0.014 inch guidewire is passed through a catheter bent into one or more 360° loops having diameters of between about 6 mm and about 12 mm. Such loops are representative of the tortuosity encountered in accessing a typical treatment site, such as the middle cerebral artery. In another test, the catheter is bent into a series of S-curves. As the guidewire is pushed and pulled through the loop or curve, any drag, bumps or wire flexure is observed, which may indicate a kink in the catheter, ovalization of the catheter, binding of the guidewire, or some other deleterious condition.

Kink resistance of the ultrasound catheter, which is also related to the ability to freely pass a guidewire through the catheter, can be evaluated by testing the minimum radius 180° bend that the catheter can be subjected to without kinking. In an exemplary embodiment, the catheter can be subjected to a 180° bend having a radius of about 10 mm without kinking. In another exemplary embodiment, the catheter can be subjected to a 180° bend having a radius of about 8 mm without kinking. In still another exemplary embodiment, the catheter can be subject to a 180° bend having a radius of less than or equal to about 6 mm without kinking.

The ability of the catheter to track the guidewire at a difficult region of the patient's vasculature, such as at a small radius bend or at a bifurcation, can also be evaluated. Generally, a greater force is required to navigate the catheter around a small-radius curved path than a large-radius curved path, and generally a greater force is required to navigate the catheter around a 180° curve than a curve less than 180°. For example, in one embodiment, less than approximately 10 grams are required to push an ultrasound catheter over a standard 0.014 inch guidewire around a curve having a diameter of about 7 mm. In another embodiment, less than approximately 8 grams are required to push an ultrasound catheter over a standard 0.014 inch guidewire around a curve having a diameter of about 7 mm.

Control System.

Figure 6:
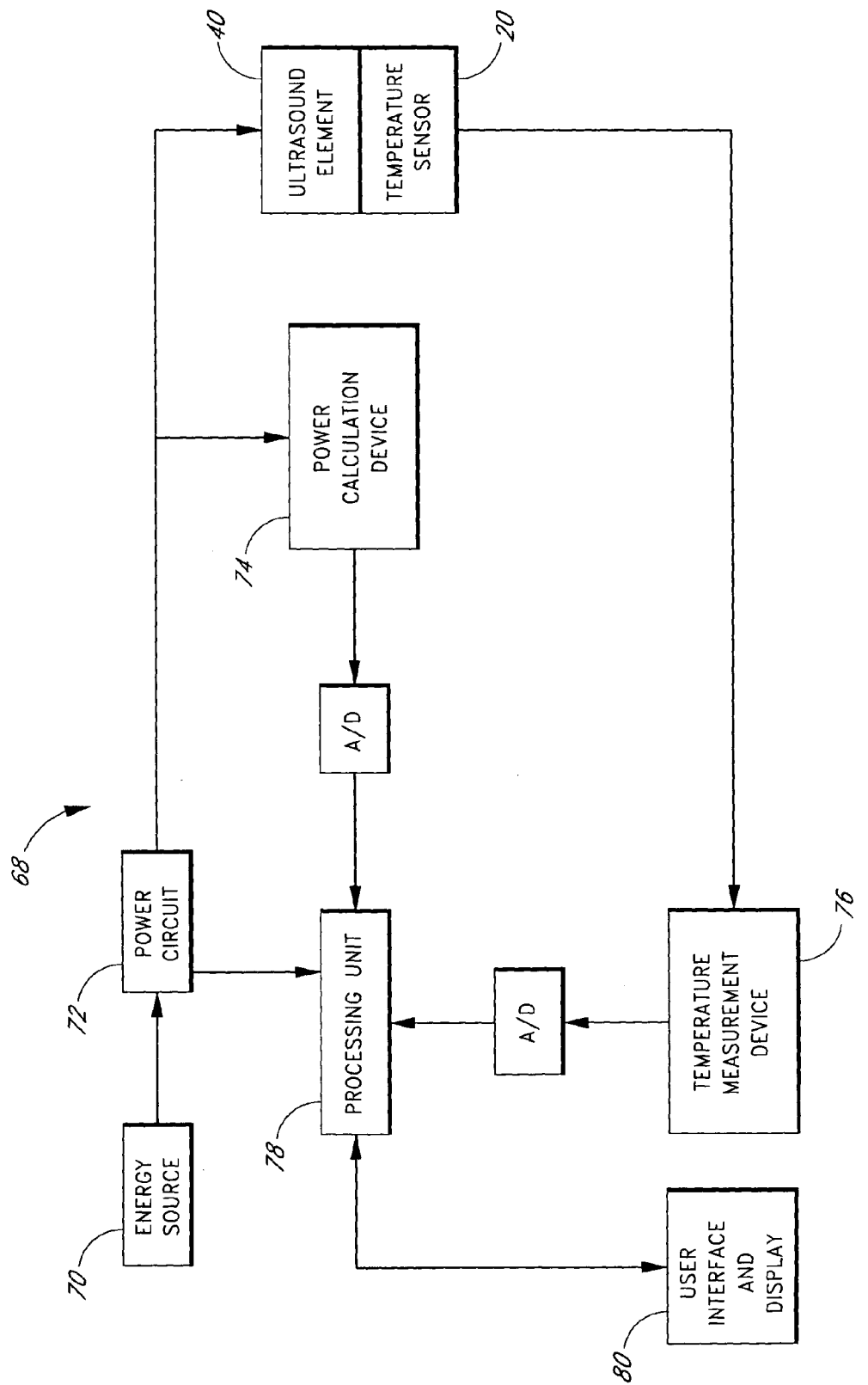
FIG. 6 is a schematic illustration of an exemplary control system for a ultrasound catheter.

FIG. 6 illustrates one embodiment of a control system 68 that can be used with the ultrasound catheters 100 described herein. In an exemplary embodiment, the control system 68 is integrated into and operatively connected to the ultrasound catheter 100 by the control box connector 120 (illustrated in FIG. 1). The control system 68 allows the temperature detected by a temperature sensor 136 to be monitored and allows the output power of an energy source 70 used to drive the ultrasound radiating member 124 to be adjusted accordingly. The control system 68 can be configured as a closed or open loop feedback system. Although one ultrasound radiating member 124 and one temperature sensor 136 are illustrated in FIG. 6, additional ultrasound radiating members and/or temperature sensors can be used in modified embodiments.

In an exemplary embodiment, the control system 68 comprises an energy source 70, power circuits 72, and a power calculation device 74 that is coupled to an ultrasound radiating member 124. A temperature measurement device 76 is coupled to a temperature sensor 128 in the ultrasound catheter 100. A processing unit 78 is coupled to the power calculation device 74, the power circuits 72 and a user interface and display 80.

In operation, the temperature at the temperature sensor 128 is determined by the temperature measurement device 76, and is provided to the processing unit 78. The determined temperature can then be displayed to the user at the user interface and display 80.

The processing unit 78 comprises logic for generating a temperature control signal. The temperature control signal is proportional to the difference between the measured temperature and a target temperature. The target temperature can be determined by the user, as set at the user interface and display 80, or can be preset within the processing unit 78.

The temperature control signal is received by the power circuits 72. In an exemplary embodiment, the power circuits 72 are configured to adjust the power level, voltage, phase and/or current of the electrical energy supplied to the ultrasound radiating members 124 from the energy source 70. For example, when the temperature control signal is above a target level, the power supplied to the ultrasound radiating member 124 is reduced in response to the temperature control signal. Similarly, when the temperature control signal is below a target level, the power supplied to the ultrasound radiating member 124 is increased in response to the temperature control signal. In an exemplary embodiment, after each power adjustment the processing unit 78 monitors the temperature sensor 136 and produces another temperature control signal which is received by the power circuits 72.

In an exemplary embodiment, the processing unit 78 further comprises safety control logic. The safety control logic detects when the temperature at a temperature sensor 128 has exceeded a safety threshold. In such embodiments, the processing unit 78 then provides a temperature control signal which causes the power circuits 72 to stop delivering energy from the energy source 70 to the ultrasound radiating member 124.

The processing unit 78 also receives a power signal from the power calculation device 74. In an exemplary embodiment, the power signal is used to determine the power received by the ultrasound radiating member 124. The determined power is optionally displayed to the user on the user interface and display 80.

As described above, in an exemplary embodiment the control system 68 is configured to maintain tissue adjacent to the ultrasound radiating member 124 below a desired temperature. For example, it is generally sought to prevent tissue at a treatment site from increasing more than 6° C. above normal body temperature.

In an exemplary embodiment, the processing unit 78 comprises a digital or analog controller, such as a computer with software. In such embodiments, the processing unit 78 can include a central processing unit ("CPU") coupled through a system bus. The user interface and display 80 can comprise a mouse, a keyboard, a disk drive, a display monitor, a nonvolatile memory system, and/or the like. In an exemplary embodiment, a program memory and a data memory is also coupled to the bus.

In lieu of the series of power adjustments described above, a preprogrammed profile of the power to be delivered to an ultrasound radiating member 124 can be incorporated into the processing unit 78, such that a preset amount of ultrasonic energy to be delivered is pre-profiled. In such embodiments, the power delivered to the ultrasound radiating member 124 can then be adjusted according to the preset profiles.

In an exemplary embodiment, the ultrasound radiating member 124 is operated in a pulsed mode. For example, in one embodiment, the time average power supplied to the ultrasound radiating member 124 is between about 0.1 watts and about 2 watts. In another embodiment, the time average power supplied to the ultrasound radiating member 124 is between about 0.5 watts and about 1.5 watts. In certain embodiments, the time average power is approximately 0.6 watts or approximately 1.2 watts. In an exemplary embodiment, the duty cycle is between about 1% and about 50%. In another exemplary embodiment, the duty cycle is between about 5% and about 25%. In another exemplary embodiment, the duty cycle is approximately 7.5% or approximately 15%. In an exemplary embodiment, the pulse averaged power is between about 0.1 watts and about 20 watts. In another exemplary embodiment, the pulse averaged power is between approximately 5 watts and approximately 20 watts. In another exemplary embodiment, the pulse averaged power is approximately 8 watts or approximately 16 watts. The amplitude during each pulse can be constant or varied.

In one embodiment, the pulse repetition rate is between about 5 Hz and about 150 Hz. In another embodiment, the pulse repetition rate is between about 10 Hz and about 50 Hz. In another embodiment, the pulse repetition rate is approximately 30 Hz. In an exemplary embodiment, the pulse duration is between about 1 millisecond and about 50 milliseconds. In another embodiment, the pulse duration is between about 1 millisecond and about 25 milliseconds. In another embodiment, the pulse duration is approximately 2.5 milliseconds or approximately 5 milliseconds.

In one particular embodiment, the ultrasound member 124 is operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

In an exemplary embodiment, the ultrasound radiating member 124 used with the electrical parameters described herein has an acoustic efficiency greater than about 50% and more preferably greater than about 75%. The ultrasound radiating member(s) 124 can be formed a variety of shapes, such as, solid cylindrical, hollow cylindrical, flat, bar, triangular, and the like.

III. Sensing Conditions at a Treatment Site

Blood Flow Reestablishment

As described above, the various embodiments of the ultrasound catheters disclosed herein can be used with a therapeutic compound to dissolve a clot and reestablish blood flow in a blood vessel. After the clot is sufficiently dissolved and blood flow is reestablished, administration of the therapeutic compound and/or ultrasonic energy can be discontinued. The therapeutic compound may cause adverse side effects if it continues to be delivered after blood flow is reestablished. Additionally, generating ultrasonic energy tends to create heat, which can damage the blood vessel. Furthermore, after blood flow has been reestablished, the treatment of the patient may need to move to another stage and/or onto another occlusion. Thus, a method and apparatus that can be used to determine when the clot has been sufficiently dissolved and/or when blood flow has been sufficiently reestablished has been developed.

As described herein, techniques have been developed for measuring and/or monitoring the degree to which a clot has been dissolved, and/or correspondingly the degree to which blood flow has been reestablished. Such information can be used to determine the effectiveness of the treatment. For example, if the blood flow is being reestablished too slowly, certain treatment parameters—such as flow rate of therapeutic compound, ultrasound frequency, ultrasound power, ultrasound pulsing parameters, position of the ultrasound radiating members, and so forth—can be adjusted or modified to increase the effectiveness of the treatment. In other instances, after blood flow is reestablished the treatment can be halted to prevent unnecessary delivery of therapeutic compound and/or ultrasonic energy. In yet another instance, information on treatment effectiveness can be used to determine if an ultrasound radiating member has malfunctioned. Thus, the methods and apparatuses disclosed herein can be used to determine the degree to which a clot has been dissolved and/or the degree to which blood flow has been reestablished.

Additionally, as disclosed herein, it is advantageous to be able to accurately position the ultrasound radiating member with respect to the clot. In particular, it is advantageous to be able to position the ultrasound radiating member at a specific location within, adjacent upstream, adjacent downstream, or otherwise near the clot. Traditional techniques for positioning an ultrasonic element with respect to the occlusion involve positioning a radiopaque marker, such as the ultrasound radiating member itself, on the medical device, injecting a contrast medium into the blood vessel and taking an angiogram. However, this technique often does not provide the necessary precision and relies on subjective visual inspections of the angiogram.

In addition, as will be explained in more detail below, methods and apparatuses for determining (a) when blood flow has been reestablished, (b) the degree to which blood flow has been reestablished and/or (c) the position of the medical device relative to the clot described below have utility outside the context of ultrasound catheters. For example, such information can be used with other technologies and techniques that are used to clear an obstruction in a blood vessel (for example, angioplasty, laser treatments, therapeutic compounds used without ultrasonic energy or with other sources of energy, and mechanical devices such as mechanical thrombectomy devices, clot grabbers, clot capture devices, clot ablation or macerator devices). Examples of such techniques are provided in U.S. Pat. Nos. 5,895,398; 6,652,536; 6,139,543; 6,090,118; 5,836,940; 5,817,144; 5,498,236; and 6,454,775. The techniques described herein can also be used with catheters configured for clot dissolution in both the large and small vasculature. An example of a catheter configured to clot dissolution in the large vasculature is provided in U.S. Patent Application Publication 2004/0024347, which is hereby incorporated by reference herein.

The methods and apparatuses for determining when blood flow has been reestablished, the degree to which blood flow has been reestablished, and/or the position of the catheter relative to the clot as disclosed herein, can be used with a feedback control system. For example, one compatible feedback control system is described herein with reference to FIG. 6. Generally, the feedback control system can be a closed or open loop system that is configured to adjust the treatment parameters in response to the data received from the apparatus. The physician can, if desired, override the closed or open loop system. In other arrangements, data can be displayed to the physician or a technician, thereby allowing the physician or technician to adjust treatment parameters and/or make decisions as to the treatment of the patient.

In one embodiment, one or more temperature sensors positioned on or within the catheter are used to detect and/or measure the reestablishment of blood flow at a clot dissolution treatment site. The temperature sensor can be used to measure and analyze the temperature of the cooling fluid, the therapeutic compound and/or the blood surrounding the catheter. For example, in one arrangement, temperature sensors mounted on the outside of the catheter, on the ultrasound radiating member, or in a catheter fluid lumens detect differential temperatures of the blood, cooling fluid, or therapeutic compound along the catheter length as a function of time.

Certain embodiments for using thermal measurements to detect and/or measure the reestablishment of blood flow during a clot dissolution treatment are illustrated schematically in FIGS. 7 and 8. An ultrasound catheter 100 is positioned through a clot 90 at a treatment site 88 in a patient's vasculature 86. The catheter 100 includes at a thermal source 150 and a thermal detector 152. In the illustrated embodiment, the thermal detector 152 is located downstream of the thermal source 150. In other embodiments, the thermal detector 152 is located upstream of, axially adjacent to, near, or coupled to the thermal source 120.

The thermal source 150 and thermal detector 152 can be positioned on, within, or integral with the catheter 10. The thermal source 150 comprises a source of thermal energy, such as a resistance heater. For example, in one embodiment, an ultrasound radiating member 124 can function as a source of thermal energy. However, the techniques disclosed herein can also be used with a catheter that does not comprise an ultrasound radiating member. The thermal detector 152 comprises a device capable of detecting the presence (or absence) of thermal energy, such as a diode, thermistor, thermocouple, and the like. In one embodiment, an ultrasound radiating member can be used as a thermal detector by measuring changes in the electrical characteristics of the ultrasound radiating member, such as, impedance or resonating frequency.

In such embodiments, the thermal source 150 supplies thermal energy into the surrounding environment, such as the surrounding bloodstream, the catheter cooling fluid lumens or the catheter drug delivery lumens. Applicants currently believe that the rate of heat dissipation at least partially depends on the thermal conductivity of blood, clot and surrounding tissues at the treatment site 88. As the clot 90 dissolves and the blood flow increases through the treatment site 88, the rate of heat dissipation will increase and this will be indicated by a decrease in temperature.

When the thermal source 150 supplies thermal energy into the surrounding environment at the treatment site 88, a "thermal pulse" is created. If the medium into which thermal energy is supplied has a flow rate, then the thermal pulse will propagate with the medium. The thermal pulse can propagate, for example, by mass transfer (that is, due to physical movement of the heated medium, such as blood) or by thermal conduction (that is, due to thermal energy propagating through a stationary medium, such as the clot).

In an exemplary embodiment, as the thermal pulse propagates downstream, the characteristics of the thermal pulse change. For example, some of the thermal energy in the thermal pulse will dissipate into surrounding tissues and/or surrounding catheter structures, thereby reducing the intensity of the thermal pulse. Additionally, as the thermal pulse passes through and/or reflects from various materials, such as clot, blood, tissue, and so forth, the pulse width can increase. This effect is illustrated schematically in FIGS. 9 and 10. When the thermal pulse reaches the thermal detector, its characteristics can be measured and analyzed, thereby providing information about blood flow at the treatment site 88.

Example: Thermal pulse delivered and measured in Bloodstream. In certain applications, a thermal pulse is delivered and measured in the patient's bloodstream at the treatment site. If the characteristics of such a thermal pulse, such as pulse width and pulse intensity, remain substantially unchanged between the thermal source and the thermal detector, this indicates that little thermal energy dissipated into surrounding tissues between the thermal source and the thermal detector. This suggests that the thermal pulse propagated rapidly, and further that there is a high blood flow rate at the treatment site.

If the same characteristics of such a thermal pulse change substantially between the thermal source and the thermal detector, such as increased pulse width or decreased pulse intensity, this indicates that a substantial amount of thermal energy dissipated into or reflected from surrounding tissues between the thermal source and the thermal detector. This suggests that the thermal pulse propagated slowly, and further that there is a low blood flow rate at the treatment site, and possibly an occluded vessel.

Example: Thermal pulse delivered and measured in catheter lumen. In applications where the thermal pulse is delivered and measured in one of the catheter lumens, reestablishment of blood flow can be evaluated based on the thermal pulse intensity reduction. Specifically, as a clot dissolution treatment progresses, less clot material will be available to absorb energy from the thermal pulse. Additionally, the thermal pulse will propagate more rapidly, providing less time for thermal dissipation. Therefore, in such applications, a high thermal pulse intensity reduction suggests that little clot dissolution has occurred, while a low thermal pulse intensity reduction indicates that the clot dissolution treatment has progressed significantly.

Additional details on the above described techniques are provided in U.S. Patent Application Publication 2003/0220568, the entire disclosure of which is hereby incorporated by reference herein.

Sensing the Position of the Obstruction

In another embodiment, temperature measurements taken at or near the treatment site 88 are used as an aid in determining blood flow reestablishment and/or the position of the catheter with respect to the clot. In one such embodiment, the thermal detector 152 is attached or coupled or positioned near the thermal source 150 (such as illustrated in FIGS. 2 and 7). In another such embodiment, the thermal detector 152 is axially spaced from the thermal source 150 (such as illustrated in FIG. 8). In one embodiment, as a clot dissolution treatment progresses, blood flow around the catheter increases, thereby increasing blood flow that serves to carry away some of the thermal energy generated by the thermal source 150. In embodiments where the average power delivered to the thermal source 150 is substantially constant, such as when the thermal source 150 is an ultrasound radiating member, thermal energy will be delivered to the treatment site 88 at a substantially constant rate. In such embodiments, if the temperature observed at the treatment site 88 is substantially constant, there exists a substantially steady-state condition between heat dissipation and heat generation.

Thus, if the thermal source 150 and the thermal detector 152 are embedded in a clot 90, the observed temperature will be different, and generally greater, than if the thermal source 150 and the thermal detector 152 are in liquid and/or flowing blood. For example, if the clot 90 is dissolved sufficiently such that blood flow around the ultrasound catheter 100 increases, or if the thermal source 150 and thermal detector 152 are removed from the clot 90—such as by pulling the ultrasound catheter 100 back from, or by pushing the ultrasound catheter 100 through, the clot—then a temperature reduction will generally be observed. Therefore, temperature changes at the treatment site 88 can be used as an aid in determining blood flow reestablishment. In a similar manner, if the control system is configured to maintain a substantially constant temperature at the treatment site, the power supplied to the thermal source can be used to determine position. In general, less power results in higher temperatures when the thermal source is positioned within the clot.

For example, in an exemplary embodiment shown in FIGS. 11-13, an ultrasound catheter 100 includes an ultrasound radiating member 124 that serves as a thermal source 150, as well as a temperature sensor 136 that serves as a thermal detector 152. The catheter is positioned such that the ultrasound radiating member 124 and the temperature sensor 136 are positioned substantially within the clot 90. As the treatment progresses and the clot 90 dissolves, blood flow around the catheter increases. This allows thermal energy generated by the ultrasound radiating member 124 to be removed from the treatment site by the flowing blood, and therefore the temperature detected by the temperature sensor 136 decreases. This temperature decrease can be displayed graphically (such as in a plot of temperature as a function of time) or alphanumerically by the user interface and display 80, thereby allowing a user to observe the temperature change. In other embodiments, the control system 68 includes preset or predetermined parameters based upon empirical or calculated data which transmit a signal to the user via the user interface and display 80 when the temperature change indicates reestablishment of blood flow.

In another embodiment, schematically illustrated in FIGS. 11-13, temperature readings are used to position the ultrasound catheter 100 with respect to the clot 90. In such embodiments, the ultrasound catheter 100 is moved towards the clot 90 over a guidewire (not shown) while emitting ultrasonic energy (see position A, illustrated in FIG. 11). The temperature readings taken near or on the ultrasound radiating member 124 can help the clinician move the ultrasound catheter 100 with respect to the clot 90. For example, when the ultrasound radiating member 124 are advanced into the clot 90 (see position B, illustrated in FIG. 12), thermal energy is moved away from the ultrasound catheter 100 relatively slowly, and a temperature increase is detected. This allows the position of the ultrasound catheter 100 with respect to the clot 90 to be inferred. In certain embodiments, a clinician wishes to advance the ultrasound catheter 100 through the clot 90 (see position C, illustrated in FIG. 13), in which case a temperature change, such as a temperature decrease, indicates that the ultrasound radiating member 124 and/or temperature sensor 136 have moved beyond the clot 90.

Using the techniques described herein, temperature data can be used to provide information regarding the relative position of the ultrasound catheter 100 and the clot 90. Specifically, monitoring the temperature measured at or near the ultrasound radiating member 124 as the ultrasound catheter 100 is advanced through a patient's vasculature 86 provides relative position information from the ultrasound catheter 100 and a clot 90. For example, FIG. 14 provides a plot of temperature as a function of time as an ultrasound catheter 100 is moved through positions A, B and C illustrated in FIGS. 11, 12 and 13, respectively.

Figure 15A:
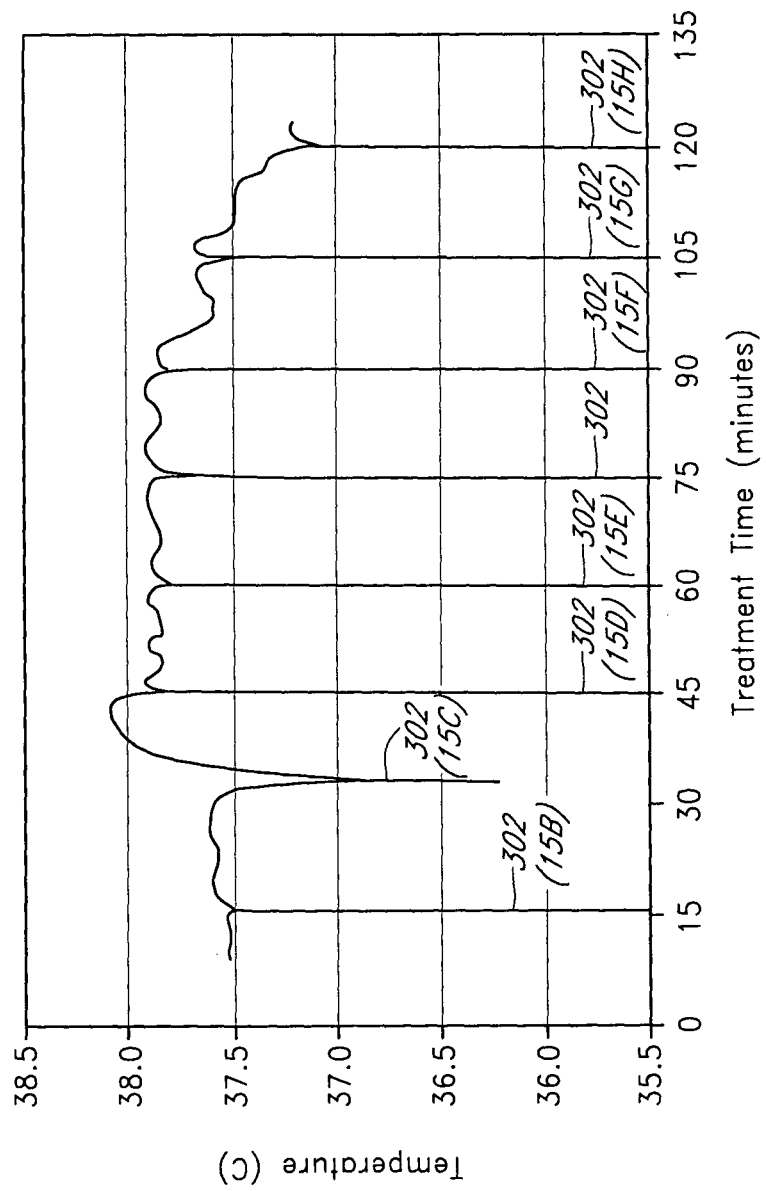
FIG. 15A is a plot of temperature as a function of treatment time of a first exemplary clot dissolution treatment.
Figure 15B:
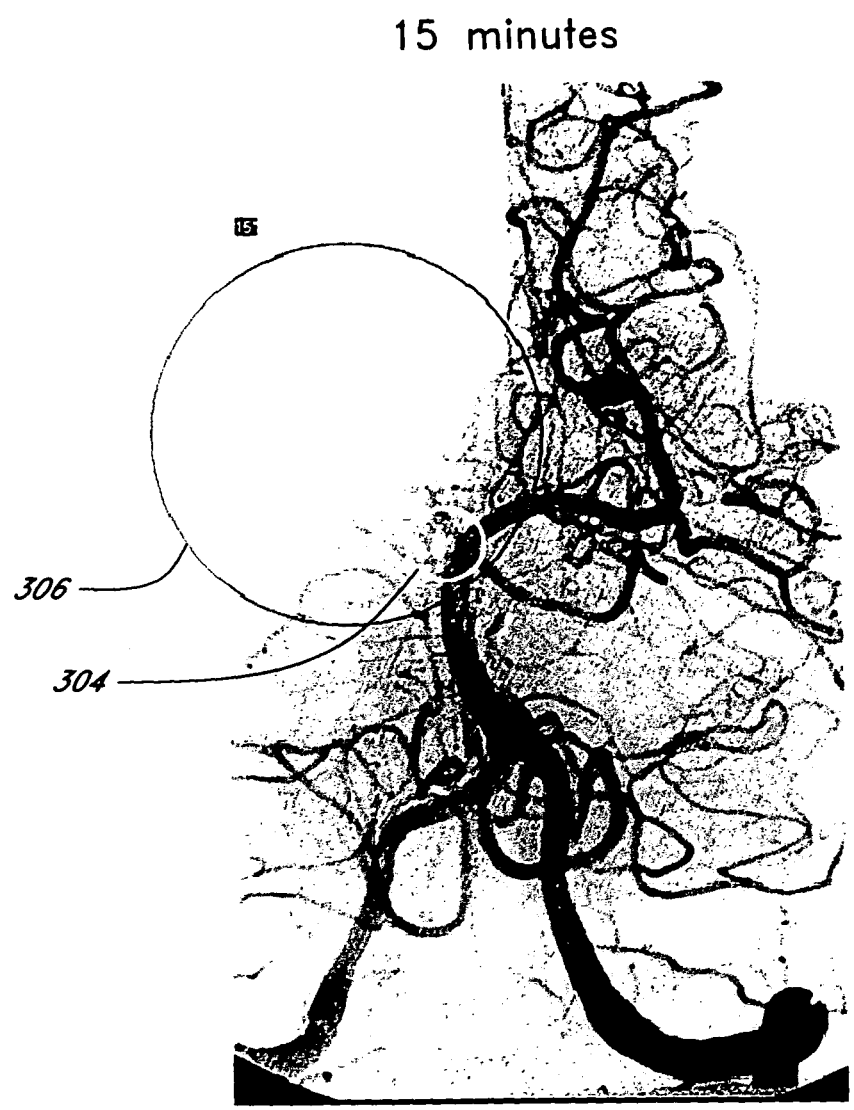
FIG. 15B is an angiogram illustrating progression of the treatment for which data are illustrated in FIG. 15A after 15 minutes.
Figure 15C:
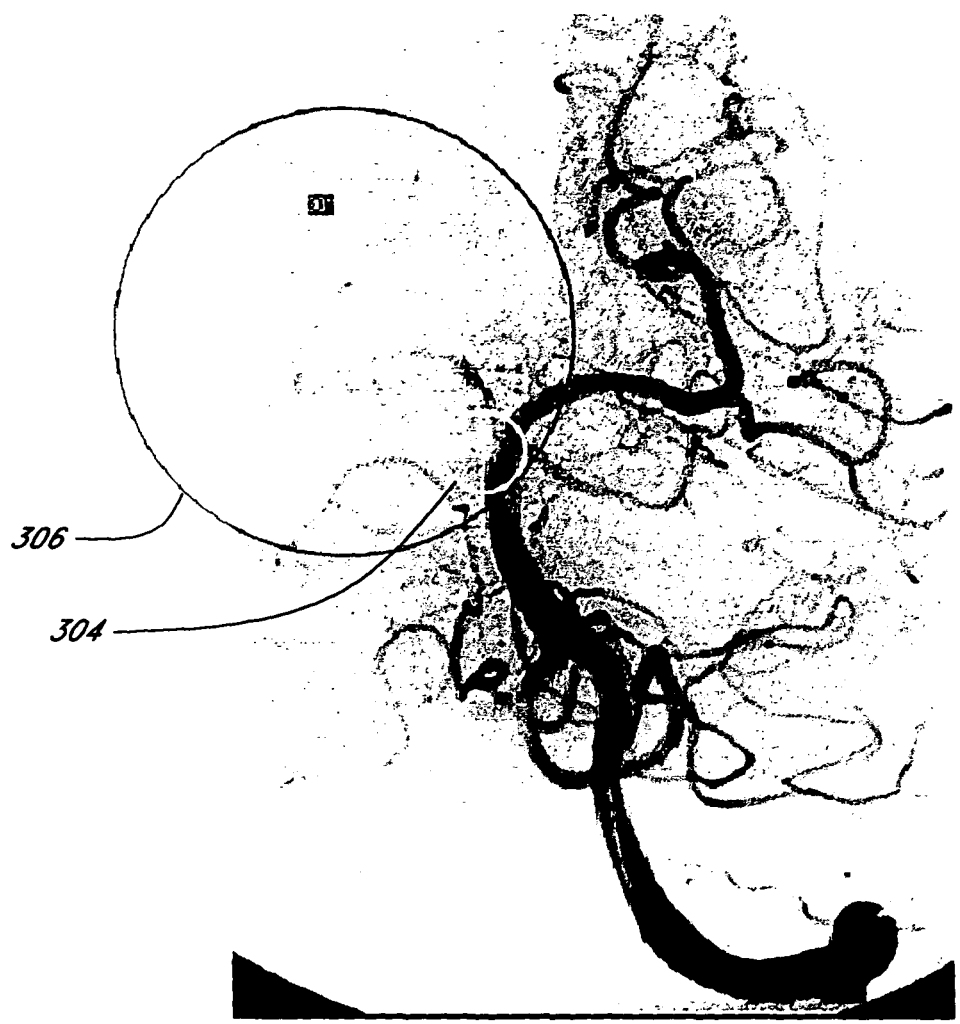
FIG. 15C is an angiogram illustrating progression of the treatment for which data are illustrated in FIG. 15A after 30 minutes.
Figure 15D:
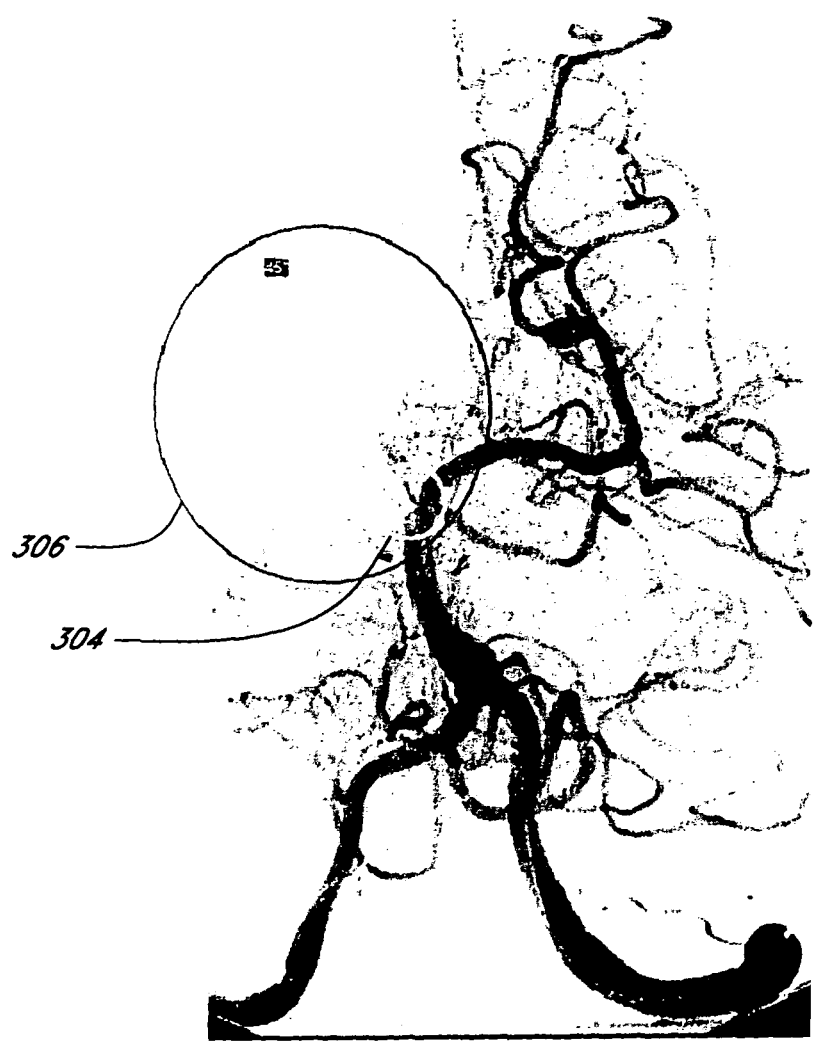
FIG. 15D is an angiogram illustrating progression of the treatment for which data are illustrated in FIG. 15A after 45 minutes.
Figure 15E:
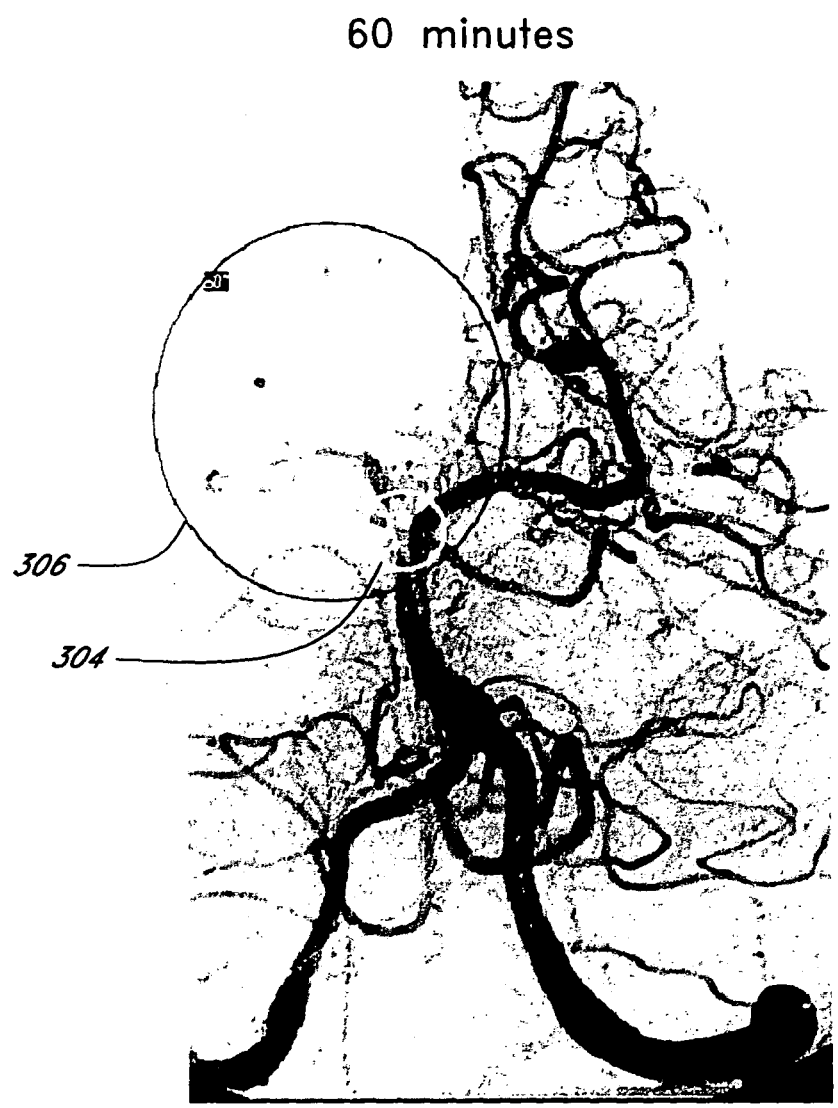
FIG. 15E is an angiogram illustrating progression of the treatment for which data are illustrated in FIG. 15A after 60 minutes.
Figure 15F:
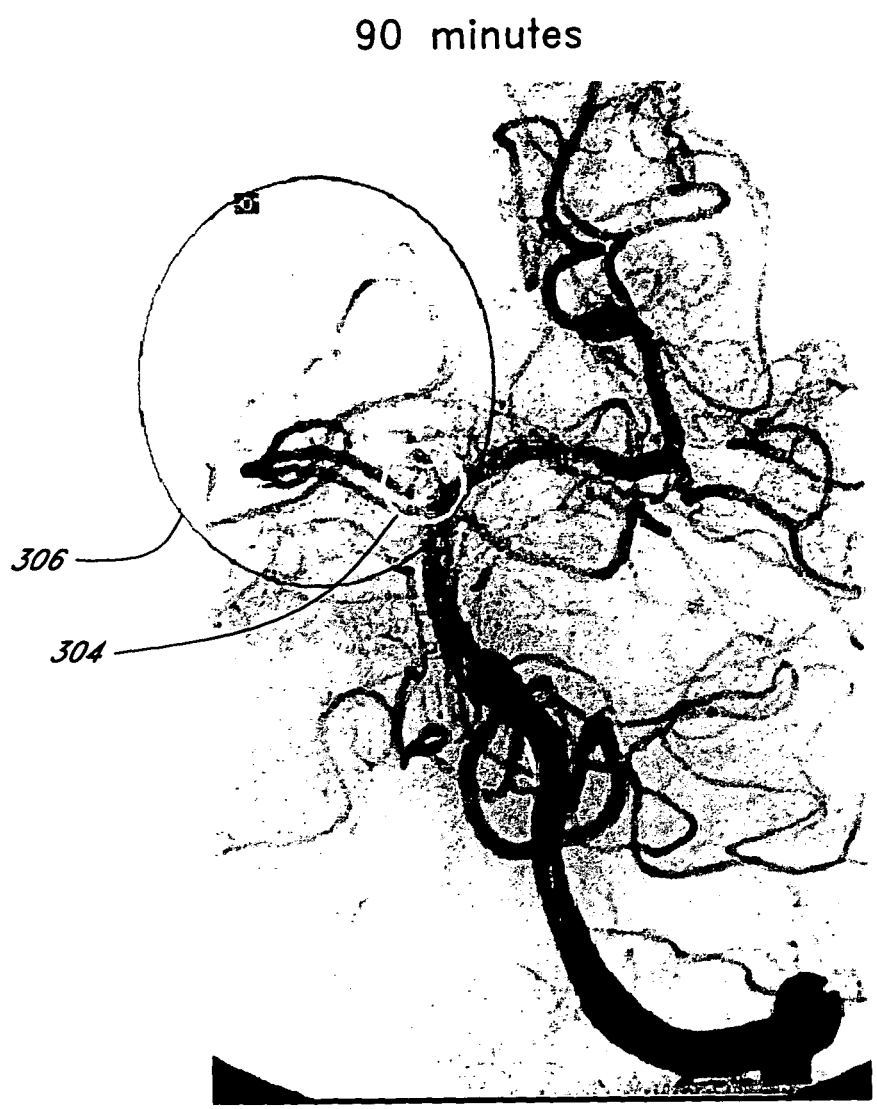
FIG. 15F is an angiogram illustrating progression of the treatment for which data are illustrated in FIG. 15A after 90 minutes.
Figure 15G:
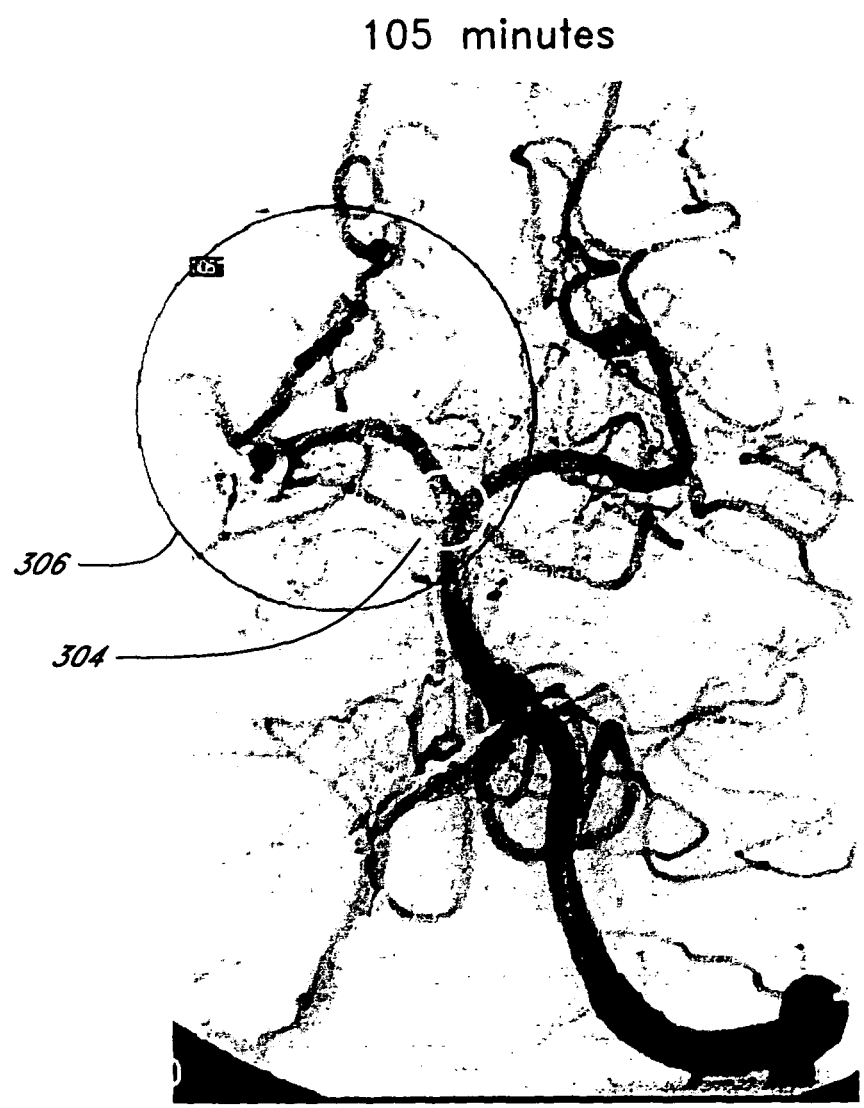
FIG. 15G is an angiogram illustrating progression of the treatment for which data are illustrated in FIG. 15A after 105 minutes.
Figure 15H:
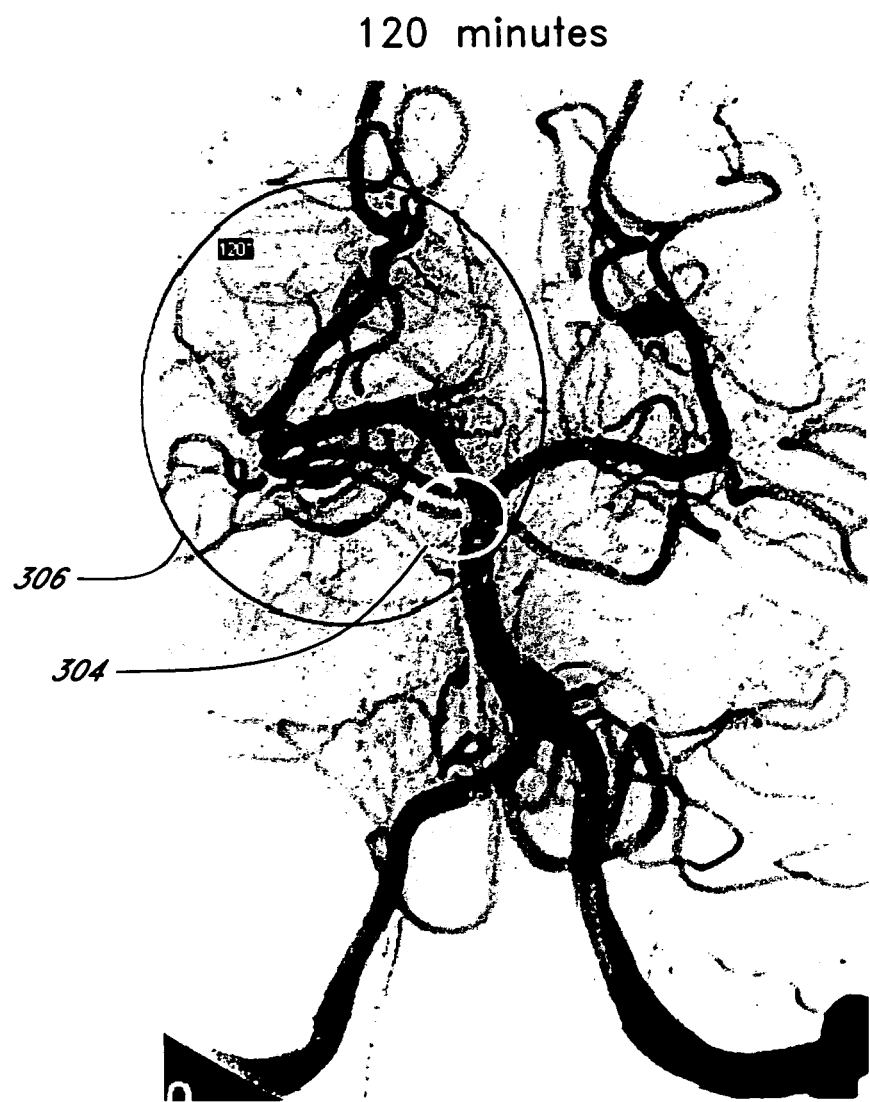
FIG. 15H is an angiogram illustrating progression of the treatment for which data are illustrated in FIG. 15A after 120 minutes.

Clinical data from a first exemplary application of the techniques disclosed herein is illustrated in FIGS. 15A-15H. In FIG. 15A, the temperature measured at a treatment site is provided as a function of treatment time. During the two hour clot dissolution treatment, the average power delivered from an ultrasound radiating member to the treatment site remained at about 0.445 watts. At approximately 15 minute intervals during the treatment, a relatively cool contrast medium was introduced to the treatment site, thereby producing the downward temperature spikes 302 evident in FIG. 15A. The contrast medium was used to produce the angiograms provided in FIGS. 15B-15H. As the blood washes away the contrast medium, the temperature of the treatment site returns to its pre-constant medium-injection level. The periodic angiograms provided in FIGS. 15B-15H indicate the presence of blood flow as darkened vessels as marked with the contrast medium, and the absence of blood flow as light or invisible vessels. The location of the radiopaque ultrasound radiating member is indicated by region 304, and the region of the vasculature to which blood flow is initially occluded is indicated by region 306.

The data presented in FIG. 15A-15H indicates that a temperature sensor positioned adjacent to the ultrasound radiating member in a small vessel catheter can provide information regarding the progression of a clot dissolution treatment. In particular, as the treatment progresses, the clot dissolves, and the blood flow rate past the ultrasound catheter increases—as evidenced by the angiograms from the latter portion of the treatment—the temperature measured at the treatment site decreases—as evidenced by FIG. 15A. Because the average power delivered from the ultrasound catheter 100 remained substantially constant during the treatment, the observed temperature decrease is a result of more thermal energy being carried away from the treatment site, for example due to increased blood flow, rather than due to a reduction in the amount of ultrasonic energy delivered to the treatment site.

Figure 16A:
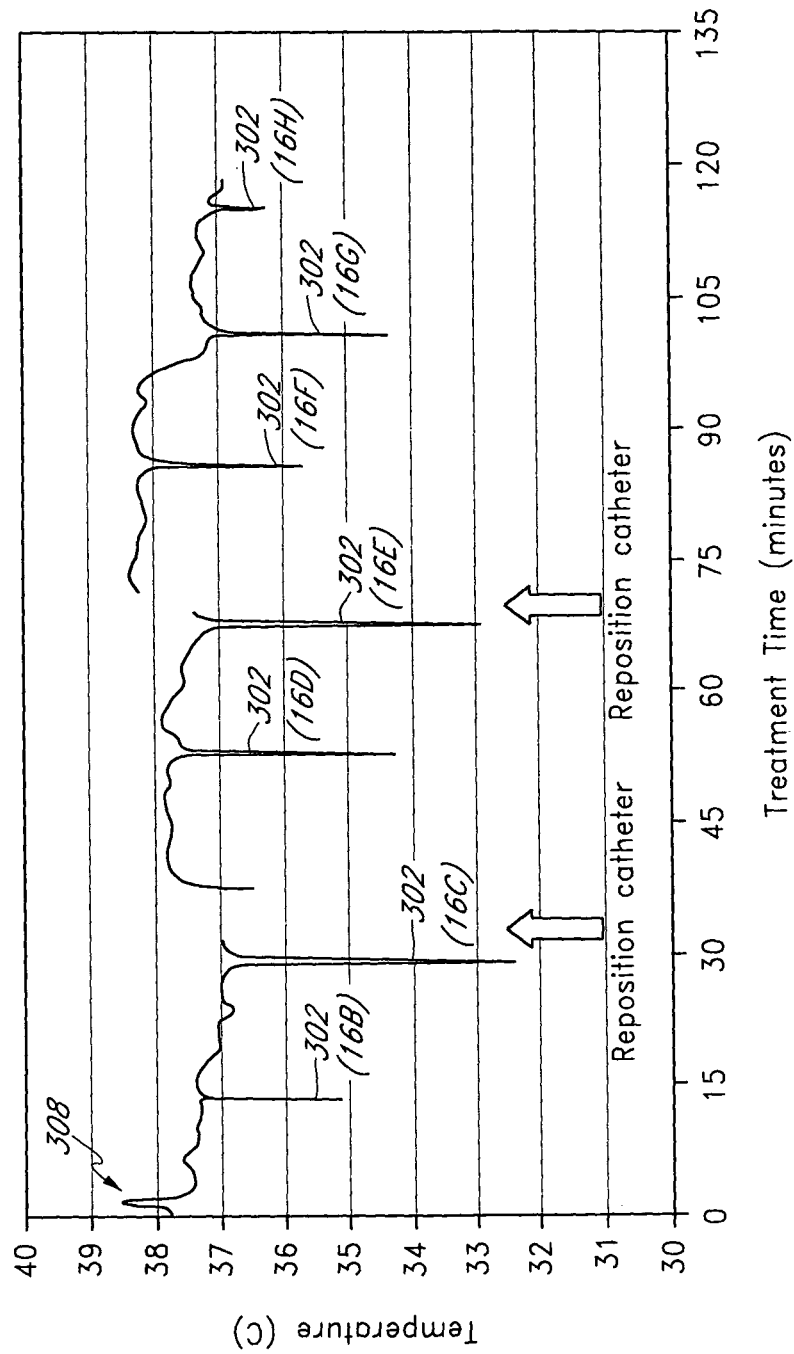
FIG. 16A is a plot of temperature as a function of treatment time of a second exemplary clot dissolution treatment.
Figure 16B:
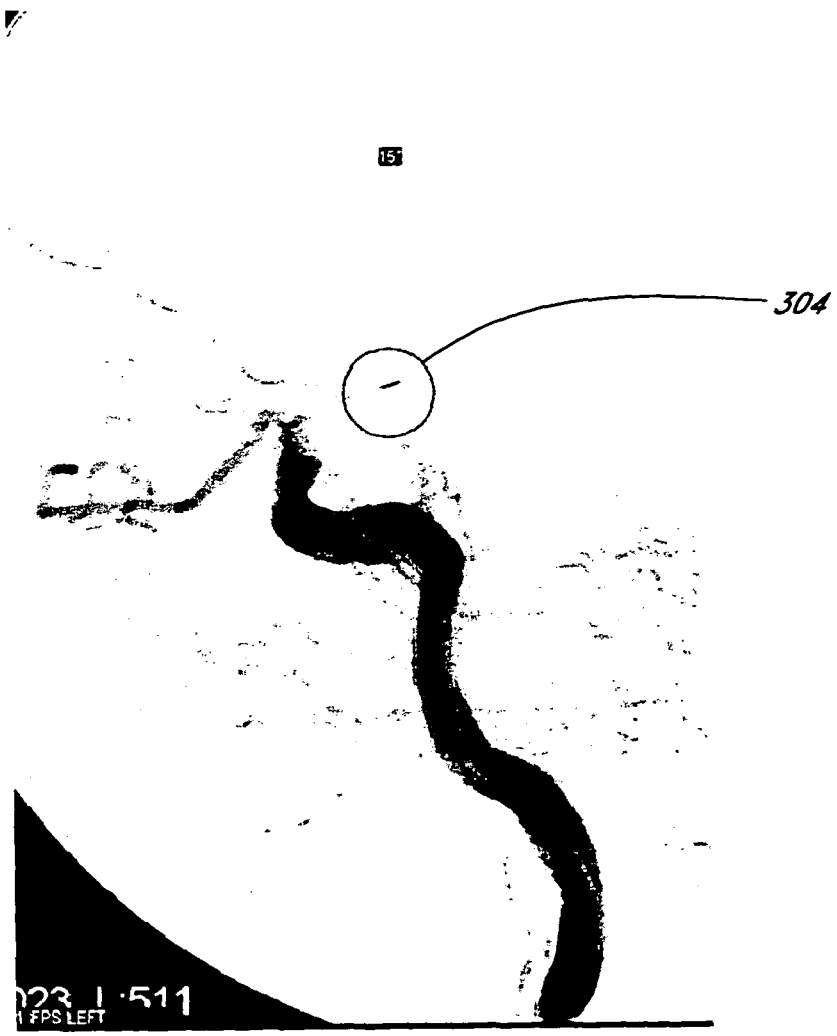
FIG. 16B is an angiogram illustrating progression of the treatment for which data are illustrated in FIG. 16A after 15 minutes.
Figure 16C:
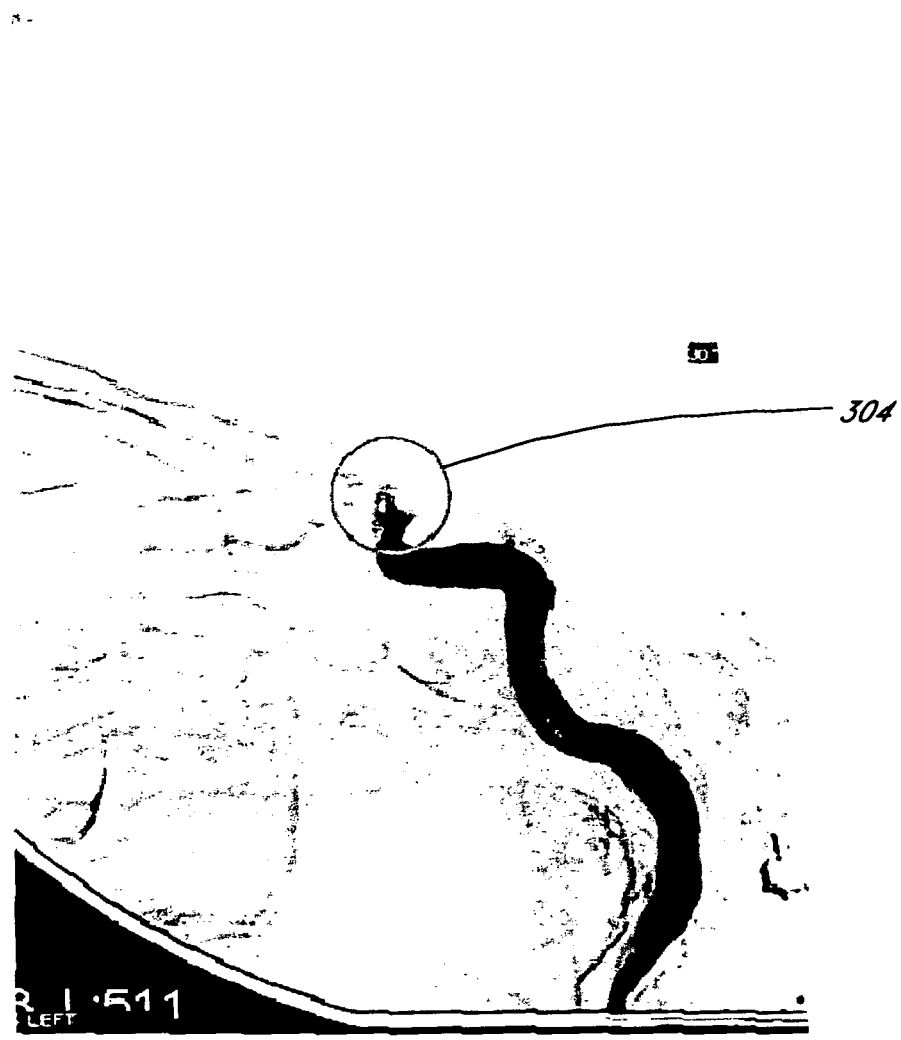
FIG. 16C is an angiogram illustrating progression of the treatment for which data are illustrated in FIG. 16A after 30 minutes.
Figure 16D:
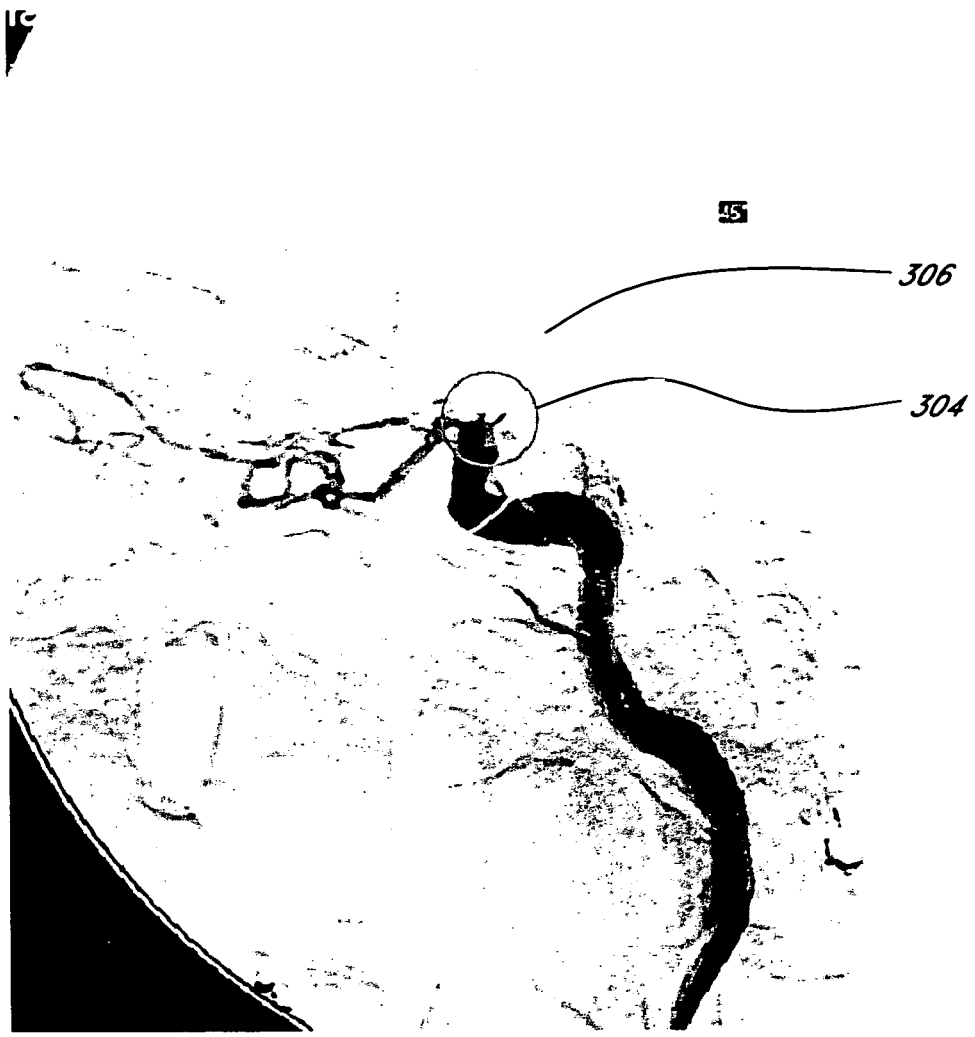
FIG. 16D is an angiogram illustrating progression of the treatment for which data are illustrated in FIG. 16A after 45 minutes.
Figure 16E:
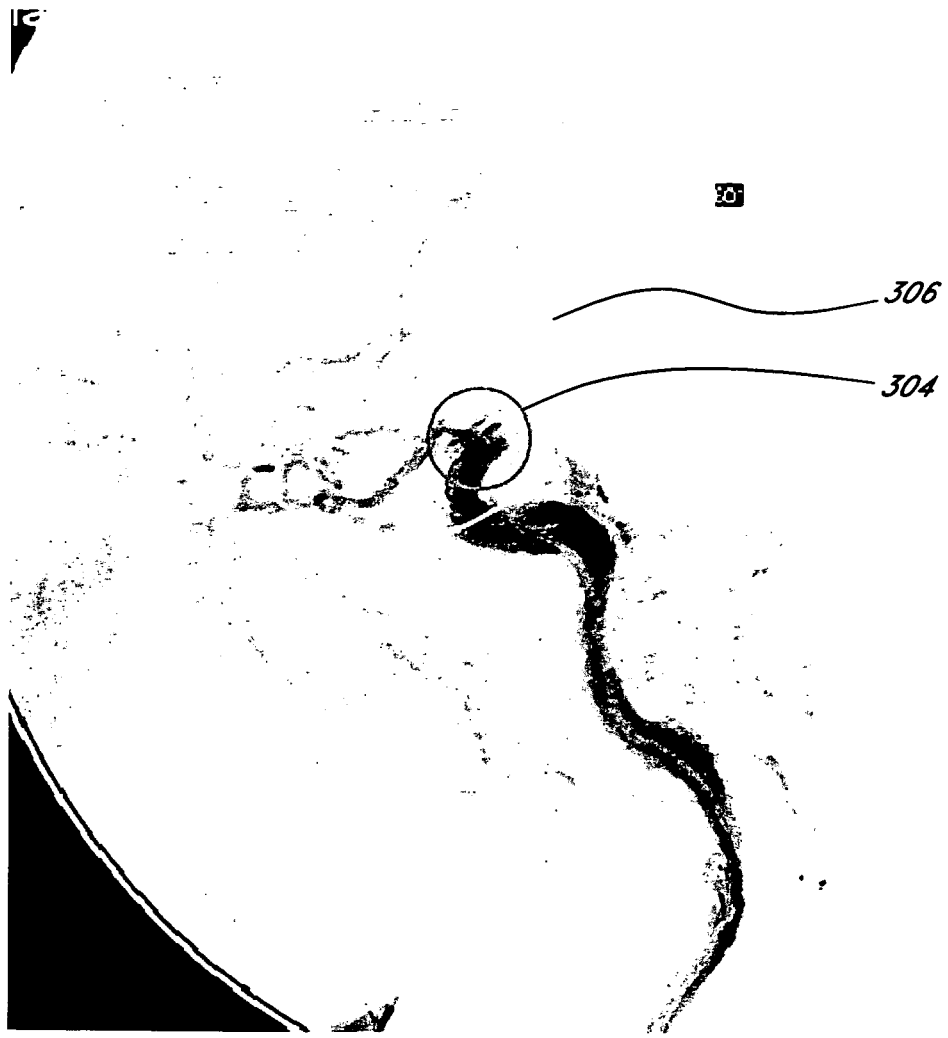
FIG. 16E is an angiogram illustrating progression of the treatment for which data are illustrated in FIG. 16A after 60 minutes.
Figure 16F:
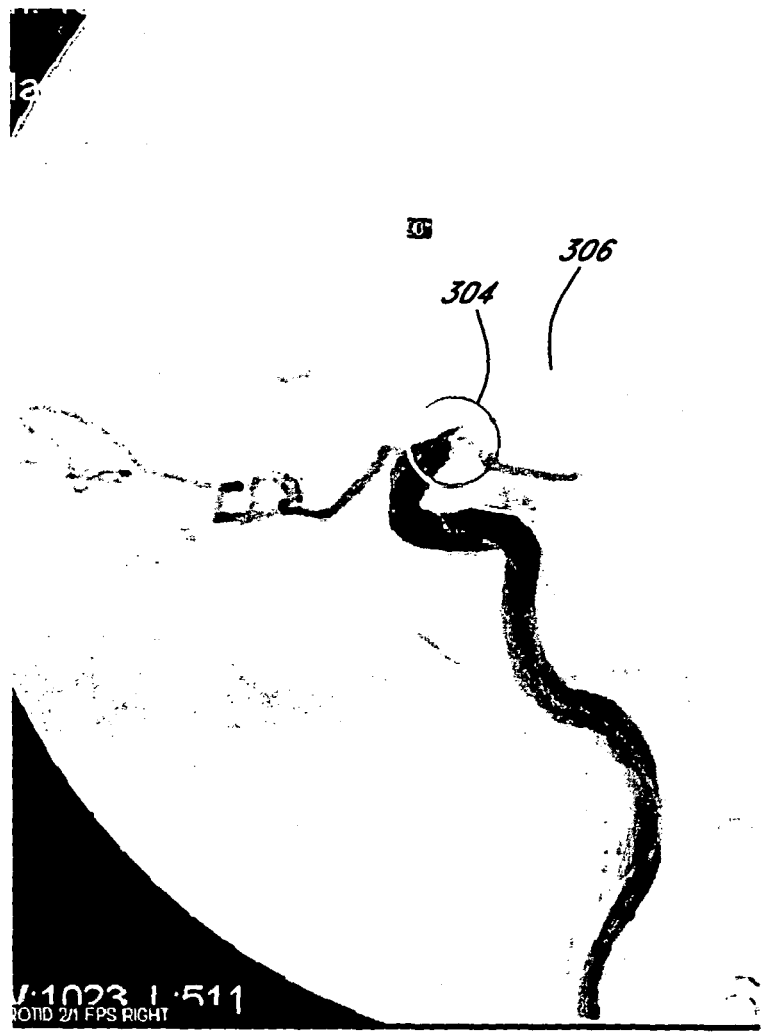
FIG. 16F is an angiogram illustrating progression of the treatment for which data are illustrated in FIG. 16A after 90 minutes.
Figure 16G:
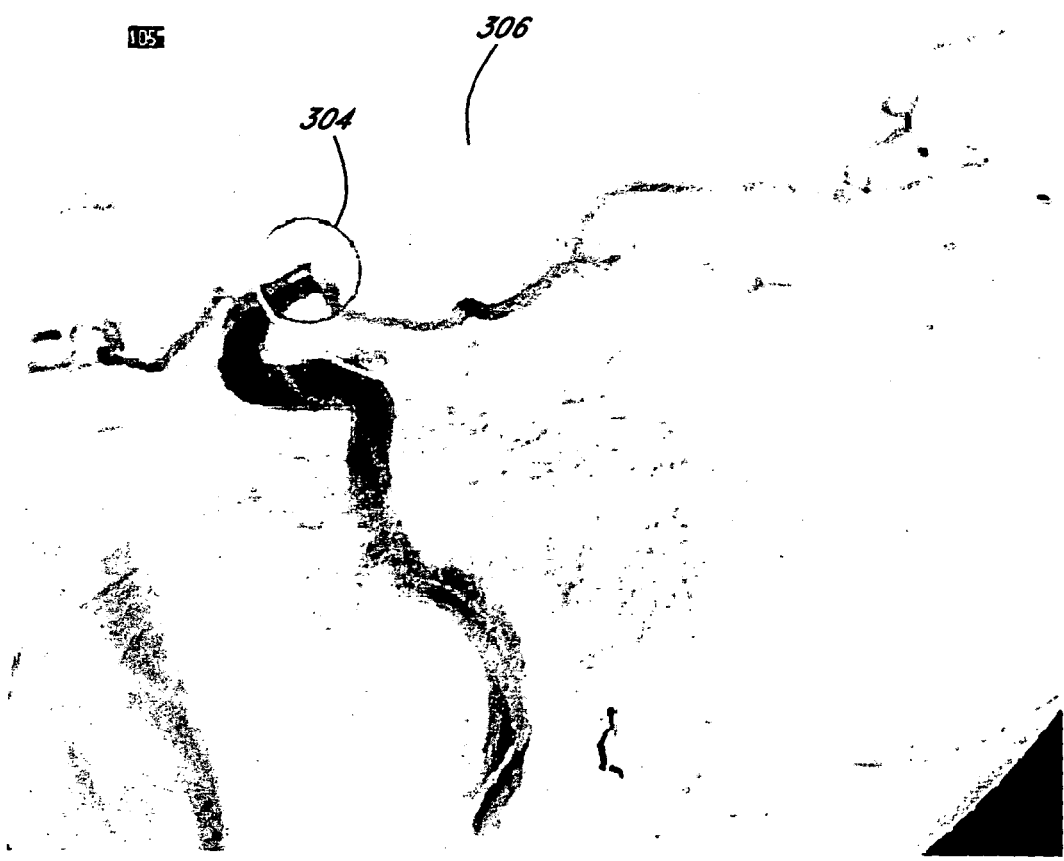
FIG. 16G is an angiogram illustrating progression of the treatment for which data are illustrated in FIG. 16A after 105 minutes.
Figure 16H:
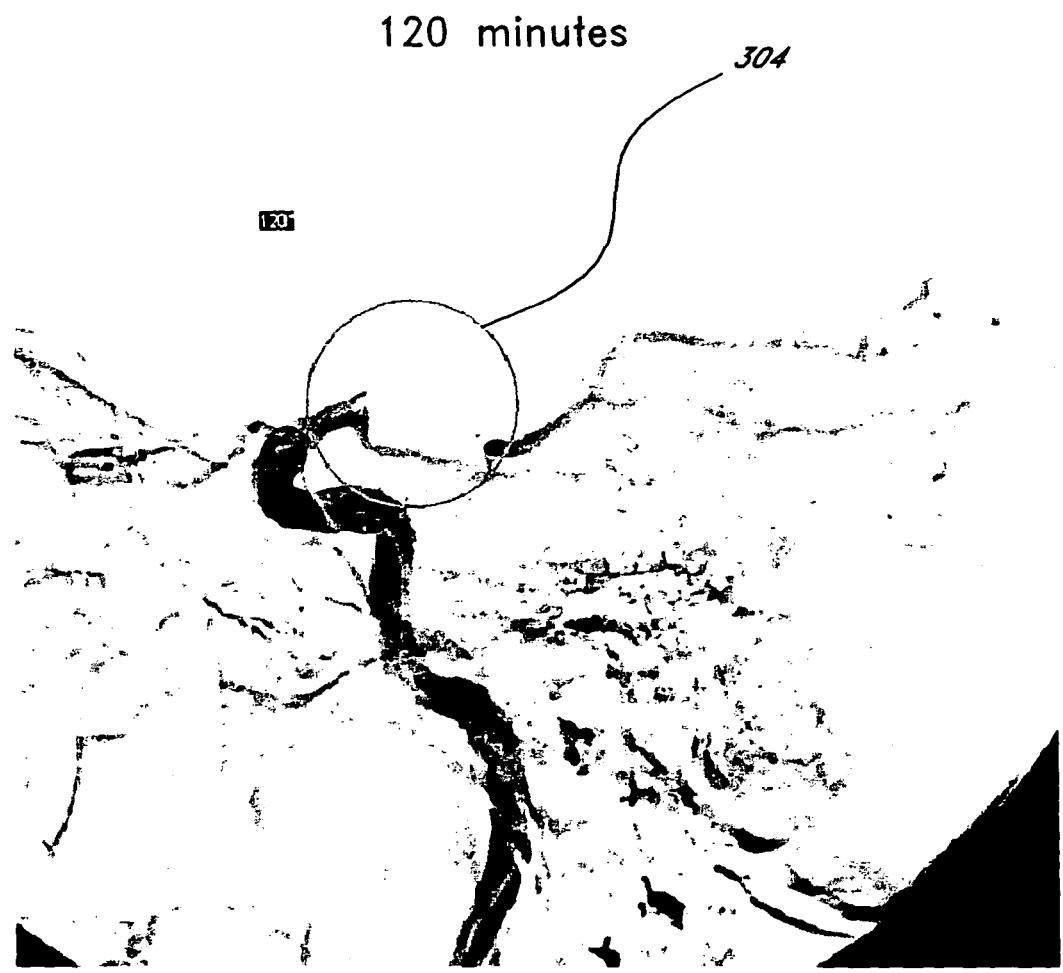
FIG. 16H is an angiogram illustrating progression of the treatment for which data are illustrated in FIG. 16A after 120 minutes.

Clinical data from a second exemplary application of the techniques disclosed herein is illustrated in FIGS. 16A-16H. In FIG. 16A, the temperature measured at a treatment site is provided as a function of time. The ultrasound catheter was repositioned twice during the treatment, as illustrated in FIG. 16A. During the two hour clot dissolution treatment, the average power delivered from an ultrasound radiating member to the treatment site remained at about 0.445 watts, at the peak power remained at about 53 watts. At approximately 15 minute intervals during the treatment, a relatively cool contrast medium was introduced to the treatment site, thereby producing the downward temperature spikes 302 evident in FIG. 16A. The contrast medium was used to produce the angiograms provided in FIGS. 16B-16H. As the blood washes away the contrast medium, the temperature of the treatment site returns to its pre-constant medium-injection level. The periodic angiograms provided in FIGS. 16B-16H indicate the presence of blood flow as darkened vessels as marked with the contrast medium, and the absence of blood flow as light or invisible vessels. The location of the radiopaque ultrasound radiating member is indicated by region 304, and the region of the vasculature to which blood flow is initially occluded is indicated by region 306.

When the ultrasound radiating member is initially positioned within the clot, a momentary temperature increase is observed, as indicated by region 308 in FIG. 16A. As described herein, this momentary temperature increase provides an indication that the ultrasound radiating member has been inserted into the clot. In certain embodiments, the ultrasound catheter is slowly advanced until a temperature increase is observed, which indicates that the ultrasound radiating member has been inserted into a clot. The catheter can then be advanced, withdrawn or held stationary depending upon the desired position of the catheter relative to the clot.

As described herein, the information from the temperature sensor cab be used in a variety of ways by the control system 68 assist the user in determining (a) when blood flow has been reestablished, (b) the degree to which blood flow has been reestablished and/or (c) the position of the ultrasound catheter 100 relative to the clot. Temperature data, such as that illustrated in FIGS. 15A and 16A, can be displayed graphically or alphanumerically as a function of time on the user interface and display 80. In a modified embodiment, the control system uses empirical and/or calculated data to interpret the temperature data for the user and generate an alarm and/or signal indicating the progress of the treatment and/or the position of the catheter.

As mentioned above, the systems and methods described herein have utility outside the context of ultrasonic catheters. For example, a device other than an ultrasound radiating member, such as a resistance heater, can be used to supply thermal energy to the treatment site. Furthermore, non-thermal techniques can be used to sense fluid flow rates at a treatment site. Generally, an increase in flow rate at the treatment site indicates dissolution of an obstruction. Examples of flow sensors compatible with the applications disclosed herein include thin film flow sensors that are embedded on or within the surface of the catheter.

Figure 17C:
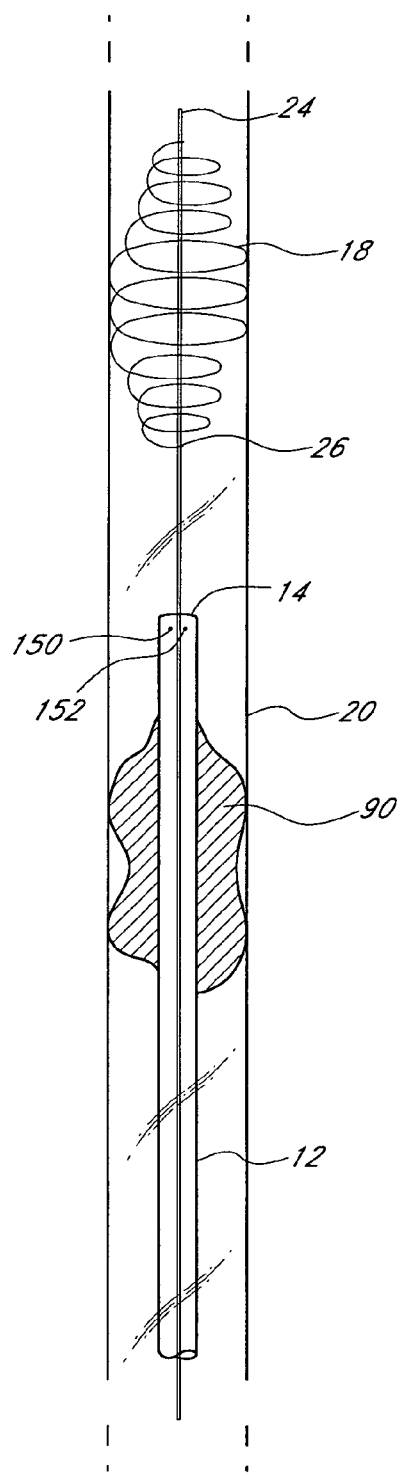
FIG. 17C is a schematic illustration of the deployment of the clot capture device of FIG. 17A.

As illustrated in FIGS. 17A-17F, a thermal source 150 and thermal detector 152 can be used with a clot capture device 10. In FIG. 17A, a clot capture device 10 is generally illustrated within a vessel 20 that is occluded by a clot 90. The clot capture device 10 comprises a catheter 12 having at least one lumen 14, a clot capture coil 18, and an insertion mandrel 16.

In an exemplary embodiment, the catheter 12 is a commercially available catheter made from an appropriate biologically compatible material. For example, in one embodiment, the catheter has a single lumen 14 and is made from a flexible elastomeric material such as silicone, rubber, polyvinyl chloride, polyurethanes, polyesters, PTFE, and the like. In an exemplary embodiment, the catheter has sufficient flexibility and length to navigate through the patient's vasculature to the occluded vessel 20 where clot 90 is located.

In one embodiment, the catheter 12 has a length between about 20 cm and about 175 cm. In one embodiment, the outer diameter of the catheter is between about 2 French to about 10 French. In one embodiment, the inner diameter is between about 1 French and about 9 French. One French is about equal to 0.013 inches.

In an exemplary embodiment, the insertion mandrel 16 has sufficient stiffness such that it can support the clot capture coil 18. In one embodiment, the insertion mandrel 16 comprises stainless steel and is a solid wire having a diameter between about 0.006 inches and about 0.038. In other embodiments, the insertion mandrel 16 comprises a hard plastic, nitinol, or other similar materials. In an exemplary embodiment, the insertion mandrel 16 is approximately between about 10 cm and about 20 cm longer than the catheter. This allows the operator of the device to control the insertion mandrel 16 by gripping a proximal end that extends from a proximal end of the catheter 12.

In an exemplary embodiment, the thermal source 150 and the thermal detector 152 are positioned near or adjacent a distal end of the catheter, as illustrated in FIG. 17A. However, in modified embodiments, these components are positioned in a more proximal portion of the catheter 12.

As described herein, the clot capture coil 18 is connected to the insertion mandrel 16. In one embodiment, the coil comprises a flexible solid elastic or super elastic material which has shape memory. As used herein, a material with "shape memory" refers, in addition to its ordinary meaning, to a material that can deform to a straight position and then return to a resting coil configuration. In an exemplary embodiment, the clot capture coil 18 comprises a solid nitinol wire with a diameter of about 0.001 inches to about 0.038 inches. Nitinol has advantageous super elasticity and shape memory properties. However, the clot capture coil 18 can also comprise other solid materials that are elastic or super elastic and that have shape memory, such as some synthetic plastics, metallic alloys, and the like.

In one embodiment, to make the clot capture coil 18, a nitinol wire is wrapped around a mandrel into the coil configuration. The nitinol is then heated to an appropriate temperature such that the nitinol wire adopts the coil configuration as its resting shape upon cooling. The diameter of the coils can vary depending on the size of the occluded vessel to be treated. In one embodiment, the diameter of the clot capture coil 18 ranges from about 1 mm for small vessels to about 30 mm for large vessels, such as the pulmonary arteries or inferior vena cava. The length of the clot capture coil 18 typically ranges from about 3 mm to about 100 mm in the proximal to distal direction, although other lengths can be used in other embodiments. Because the nitinol coil is super elastic, the coil can be extended to a completely straight configuration with the use of minimal force while retaining the capability to reform to its natural resting configuration when the force is removed. In an exemplary method of use, the clot capture coil 18 is extended by using the insertion mandrel 16 to insert both items into the narrow lumen 14 of the catheter 12.

In another embodiment, the clot capture coil 18 comprises a solid biphasic material that changes shape upon heating or the passage of electric current. For example, in one embodiment, the clot capture coil 18 comprises biphasic nitinol which has a straight configuration initially, and changes to an appropriate coiled configuration upon the passage of electric current or heating. The biphasic coil can be constructed such that the initial coil configuration is the normal shape and that the biphasic coil straightens upon passing electric current or heating. In such embodiments, the coil dimensions are similar to the dimensions expounded herein for the shape memory coil.

The coil section of either the shape memory coil or the biphasic coil can have many different configurations. In the embodiment illustrated in FIG. 17A, the clot capture coil 18 is barrel-shaped, such that the diameter is relatively small at the distal and proximal ends of the clot capture coil 18 and is relatively large in the center of the clot capture coil 18. In an exemplary embodiment, the diameter of the coil ranges from about 2 mm at the proximal and distal ends and expands to about 10 mm in the center. However, other sizes are useful depending on the relative size of the occluded vessel.

Still referring to FIG. 17A, at the proximal end of the clot capture coil 18 is a small circular loop 26. In an exemplary embodiment, the circular loop 26 is placed around the insertion mandrel 16, and is slidable thereover. The distal end of the clot capture coil 18 is fixedly connected to the distal end 24 of the insertion mandrel 16. Thus, in such embodiments, the clot capture coil 18 extends proximally from the distal end 24 of the insertion mandrel 16. In an exemplary embodiment, the clot capture coil 18 is welded onto the distal end 24 of the insertion mandrel 16, although it other embodiments, other fixation techniques can be used, such as crimping, gluing, screwing into a screw type mount, and the like.

Further details of the clot capture device and are provided in U.S. Pat. Nos. 5,895,398 and 6,652,536, as well as in U.S. Patent Publication 2004/0030375. The entire disclosure of these publications is hereby incorporated by reference herein.

In one exemplary embodiment, a patient presenting symptoms of a thromboembolic disorder is examined radiographically using angiography to locate an occlusion and to confirm the diagnosis. An introducing catheter is then inserted into an appropriate vessel, usually the femoral artery or the femoral vein. A small catheter 12, such as that illustrated in FIGS. 17A-17F, is then introduced into the vessel via the introducing catheter, and is advanced using a guidewire or the like to the occluded vessel. The catheter 12 is then passed through the viscoelastic clot 90. Once the catheter 12 is in place and through the viscoelastic clot 90, the clot capture coil 18 is introduced into the catheter 12 using the insertion mandrel 16 and is advanced to the distal region of the catheter 12.

Figure 17D:
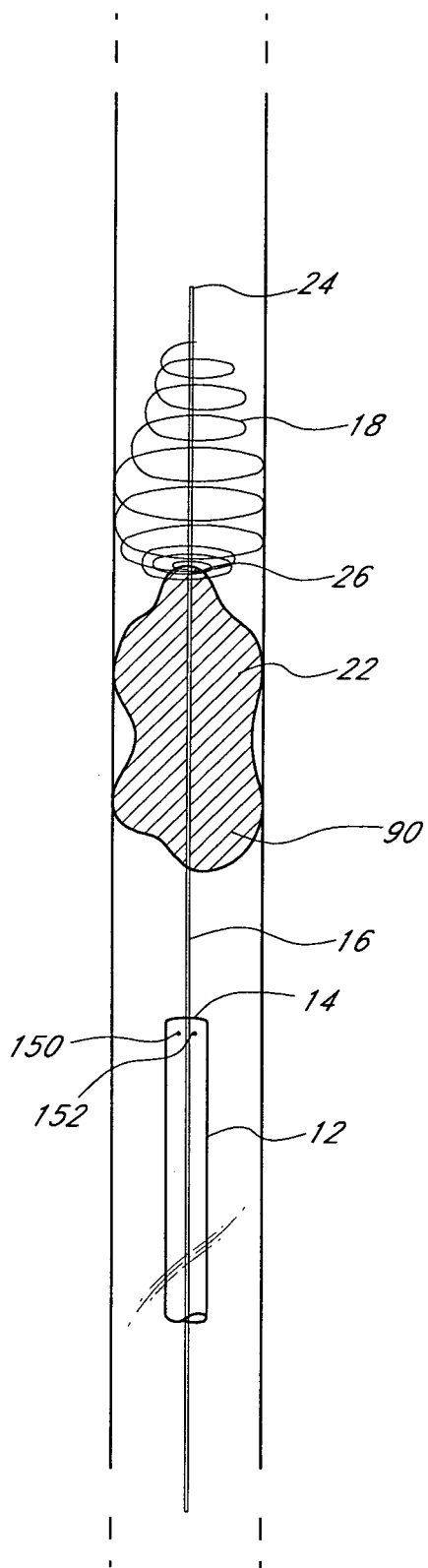
FIG. 17D is a schematic illustration of the clot capture device of FIG. 17A encountering an occlusion.
Figure 17E:
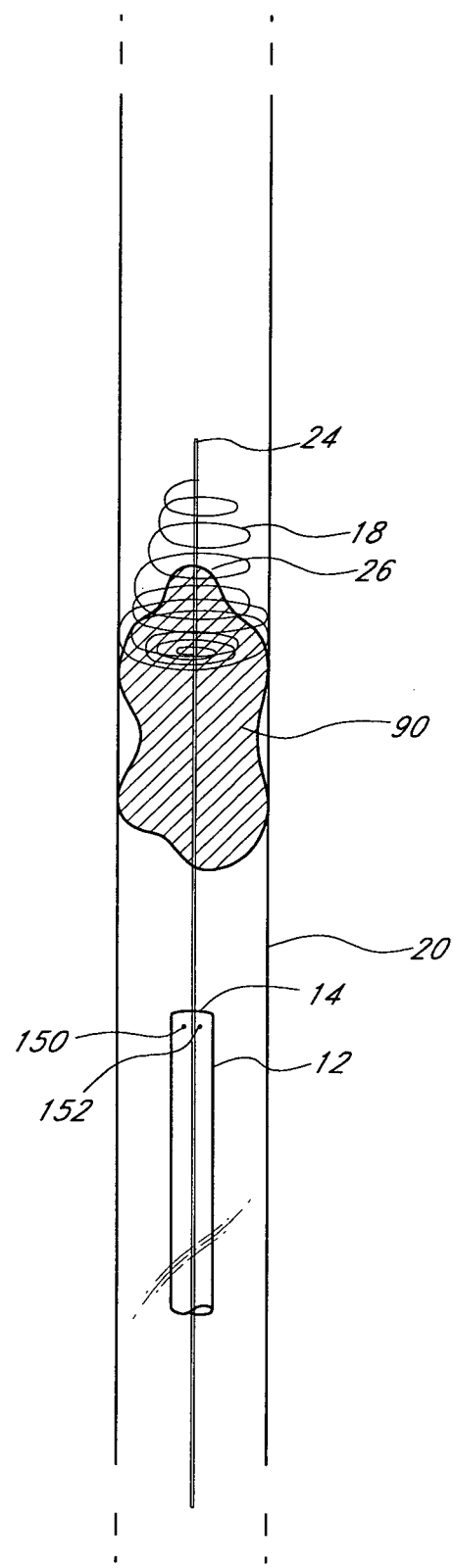
FIG. 17E is a schematic illustration of the clot capture device of FIG. 17A ensnaring an occlusion.
Figures 17F, 18:
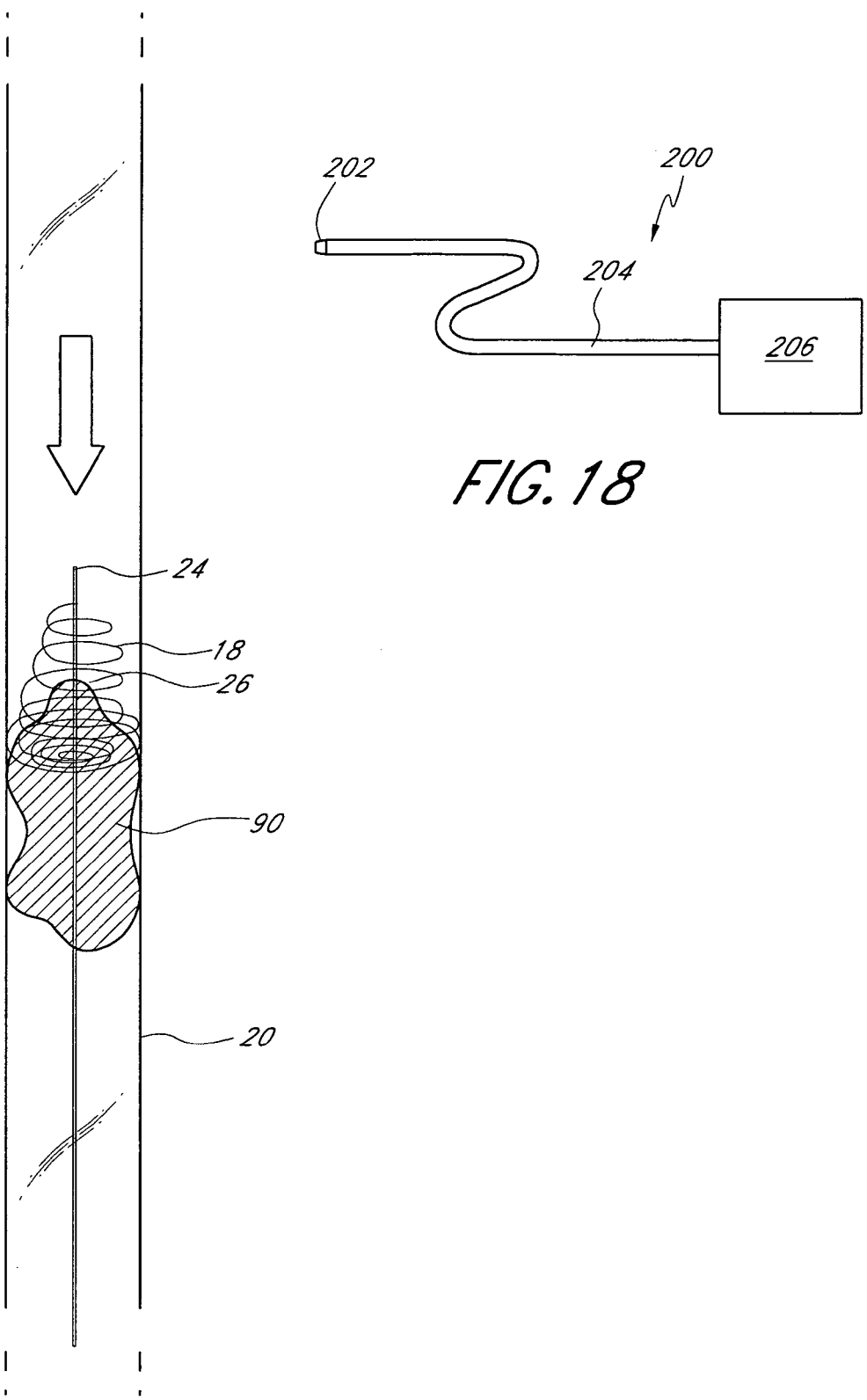
FIG. 17F is a schematic illustration of the clot of FIG. 17E being moved within an occluded artery via the clot capture coil.
FIG. 18 is a schematic illustration of a fiber optic sensor usable with certain embodiments of the catheters disclosed herein.

In an exemplary embodiment comprising a shape memory clot capture coil 18 that extends proximally from the insertion mandrel 16, the clot capture coil 18 and the insertion mandrel 16 are inserted directly into the proximal end of the catheter 12, and are advanced to the distal region of the catheter 12, as illustrated in FIG. 17B. Once the catheter 12 and the clot capture coil 18 have transversed the clot 90, the insertion mandrel 16 is translated distally relative to the catheter 12, as illustrated in FIG. 17C. The shape memory clot capture coil 18 deploys and reforms its natural configuration outside the distal end of the catheter. The clot 90 is then retrieved by translating the insertion mandrel 16 and the catheter 12 proximally, as illustrated in FIGS. 17D-17F. When the clot capture coil 18 is pulled proximally, the clot 90 becomes ensnared. Additionally, while pulling proximally on the insertion mandrel 16, the clot capture coil 18 can be rotated by rotating the insertion mandrel 16, thereby transfixing the clot 90 by corkscrewing the clot 90 into the coils of the clot capture coil 18. The viscoelastic properties of the clot 90 allow the clot 90 to be captured within the clot capture coil 18 and to be captured using the most distal coils as a capture cup. The clot 90 can then be completely removed from the patient's vasculature, or can be released into a vessel that does not perfuse a critical organ, such as an external carotid artery.

The thermal source 150 and the thermal detector 152 can be used with the clot capture coil 18 to determine the position of the clot 90. For example, as the catheter 12 is inserted into the clot 90, a temperature increase can be detected, as described herein. The temperature increase indicates that the distal region of the catheter 12 is positioned within the clot 90. As the catheter 12 is advanced further, a temperature decrease can be detected, as described herein. The temperature decrease indicates that the distal region of the catheter has passed through the clot 90. In this manner, the catheter 12 can be properly positioned behind the clot 90 before the clot capture coil 18 is deployed. In a modified embodiment, the clot capture coil 18 is deployed within or in front of the clot 90, depending on the device or technique used. In such arrangements, the catheter 12 can be first advanced into to the clot 90 by detecting a temperature change as described herein, and then can be withdrawn as described herein. The detected temperature change can also be used to determine the effectiveness of the clot removal technique.

Similarly, the apparatuses and techniques described herein can also be used with other techniques for treating an occluded vessel. For example, therapeutic compound delivery (without or without additional energy or techniques), angioplasty, laser treatments, mechanical devices (such as mechanical thrombectomy devices, clot grabbers, clot capture devices, clot ablation or macerator devices) can benefit from using a thermal source and/or sensor described above.

In a modified embodiment, the thermal source 150 and thermal detector 152 can be positioned on separate components of the catheter 12. For example, in one embodiment, the thermal source 150 is positioned on a first component (such as a catheter or a guidewire), while the thermal detector 152 is positioned on second, separate or integral, component (such as a corresponding guidewire or catheter). In still other embodiments, the thermal source 150 operates by heat removal or the addition of a cooling medium. For example, in one embodiment the thermal source 150 comprises the injection of a fluid cooler than the temperature at the treatment site and/or a cooler configured to remove heat from the treatment site. In such embodiments, the temperature change can also be used to determine the position of the clot and/or the progress of treatment. One example of such a cooling fluid is the contrast medium used to produce the downward temperature spikes 302 in FIGS. 15A and 16A.

Other Properties

As explained above, the thermal information collected by the catheters described may be used in a variety of ways to enhance the treatment of the patient. However, it is anticipated that localized measurements of other properties may also be used to enhance the treatment of the patient.

Non-limiting examples of such properties include pressure, partial pressure of various chemicals, gases and compounds in the blood (e.g., oxygen, carbon dioxide, lactic acid, free hemoglobin, and chemical markers of ischemia and/or necrosis etc.) and/or pH levels.

Various devices and techniques may be used to measure such properties. FIG. 18 illustrates one embodiment of fiber optic sensor 200. In this embodiment, the fiber optic sensor comprises a sensor element 202 that is configured to be inserted into the utility lumen of the ultrasonic catheter described above. The fiber optic sensor 200 may include one or more fiber optic fibers, which operatively connect the sensor element 202 to a detector 206 via a cable 204. The sensor 200 may be configured such that the sensor element 200 can be extended past the distal end of the catheter. In modified embodiments, the fiber optic sensor or portions thereof may be integrated into the body of the catheter.

In one embodiment, the fiber optic sensor 200 is used to determine if blood flow has been reestablished as the obstruction is dissolved or otherwise removed. For example, in one embodiment, the fiber optic sensor 200 comprises a fiber optic oxygen sensor that may use a fluorescence method to measure the partial pressure of dissolved oxygen within the blood. In such an embodiment, the increased partial pressure of oxygen indicates that blood flow is being reestablished. In a similar manner, a carbon dioxide sensor may be used to detect the partial pressure of carbon dioxide in the blood. In such an embodiment, a decrease in the amount of carbon dioxide in the blood indicates that blood flow is being reestablished. Blood pressure may also be measured by fiber optic sensors. In such an embodiment, an increase in pressure indicates that blood flow has been reestablished. Of course, those of skill in the art will recognize in light of the disclosure herein, that various other measurable parameters may also be used to determine if blood flow is being reestablished, such as, for example, pH level or other chemical compounds or precursors. Other fluorescence and reflectance spectroscopy devices may also be used. Other sensors may also be used to detect blood pressure and/or blood composition, such as, for example various electro-mechanical sensors.

In another embodiment, the fiber optic sensor 200 may be used to determine the position of the obstruction. For example, the absence of chemicals carried by blood (e.g., oxygen) may indicate that the sensor is positioned within the clot.

The fiber optic sensor 200 may also be used to detect more general conditions of the patient. Such information may then be used by the surgeon to guide therapy. For example, the fiber optic sensor may be used to detect chemical precursors which are indicative of the presence or absence of ischemic tissue or necrosis. If such precursors are sensed, a more aggressive treatment may be chosen and implemented. For example, in one embodiment, oxygenated fluid and/or hypothermia fluid may be injected past the obstruction.

In another embodiment, the sensor 200 may be used to determine the character of the obstruction itself. For example, with respect to clot material, there are differences between old and fresh clots, hard and soft clot material and clots that comprise platelets versus fibrin. These difference may suggest different treatment strategies for the different types of clots. Accordingly, the therapeutic procedure may be modified based upon the sensed condition of the clot.

In one embodiment of use, the ultrasound catheter is advanced over a guidewire through the patient's neurovascular system to the treatment site. The guidewire is then removed and the sensor 200 is then advanced through the catheter until its distal end is near or beyond the distal tip of the catheter. The condition of the treatment site may then be sensed as described above and appropriate therapeutic decisions may be made. The device may be removed from the catheter before treatment or remain in the catheter. The condition may be sensed at a later time to determine the progress of treatment.

As mentioned above, the apparatus and method for sensing the condition at a treatment site may be used in combination with an ultrasonic catheter as described herein. However, in modified embodiments, the apparatus and method may be used with an ultrasound catheter configured to treat other portions of the patient's vascular system (e.g., the peripheral vascular system). In addition, in other embodiments, the apparatus and method for sensing the condition at the treatment device may be used in combination with other treatment devices and techniques, such as, for example, drug delivery catheters and/or other techniques for removing clots.

While the foregoing detailed description has set forth several exemplary embodiments of the apparatus and methods disclosed herein, the above description is illustrative only and is not limiting of the disclosed invention. The specific dimensions and configurations disclosed can differ from those described above, and the methods described herein can be used not only within blood vessels, but within biological conduits generally.

We claim:

1. A method comprising:
   positioning a catheter within a patient's vasculature, wherein the catheter includes a thermal source and a thermal detector;
   delivering thermal energy to the patient's vasculature from the thermal source;
   making a plurality of temperature measurements near or at the thermal source using the thermal detector as the catheter is advanced through the patient's vasculature while delivering thermal energy; and
   using the temperature measurements to determine the position of the catheter with respect to a blockage in the patient's vasculature.

2. The method of claim 1, wherein delivering thermal energy to the patient's vasculature from the thermal source comprises delivering ultrasonic energy.

3. The method of claim 1, further comprising displaying the temperature measurements on a display.

4. The method of claim 1, further comprising performing a medical treatment configured to reduce the blockage.

5. The method of claim 1, further comprising performing a medical treatment configured to reduce the blockage, wherein the medical treatment includes delivering ultrasonic energy and a therapeutic compound from the catheter to the patient's vasculature.

6. The method of claim 1, further comprising performing a medical treatment configured to reduce the blockage, wherein the medical treatment comprises deploying a clot capture device from the catheter.

7. The method of claim 1, wherein the thermal energy is being delivered while the catheter is advanced through the patient's vasculature.

8. The method of claim 7, wherein the thermal energy is ultrasound energy.

* * * * *